United States Patent [19]
Mann et al.

[11] Patent Number: 5,833,623
[45] Date of Patent: Nov. 10, 1998

[54] SYSTEM AND METHOD FOR FACILITATING RAPID RETRIEVAL AND EVALUATION OF DIAGNOSTIC DATA STORED BY AN IMPLANTABLE MEDICAL DEVICE

[75] Inventors: Brian M. Mann, Edgartown, Mass.; Joseph J. Florio, La Canada, Calif.; Jason A. Sholder, Towaco, N.J.; Leslie S. Miller, Acton, Calif.; Jeffery D. Snell, Oak Park, Calif.; Kenneth Valikai, Palos Verdes Pen., Calif.; Gregory Bevan, Canyon Country, Calif.; J. Kelly Fox, Lake Jackson, Tex.; Azita M. Rahbari; Allan R. Schwartz, both of Moorpark, Calif.

[73] Assignee: Pacesetter, Inc., Sylmar, Calif.

[21] Appl. No.: 851,059

[22] Filed: May 5, 1997

Related U.S. Application Data

[60] Provisional application No. 60/015,503, May 14, 1996.
[51] Int. Cl.[6] .................................................. A61B 5/044
[52] U.S. Cl. ............................................. 600/523; 607/32
[58] Field of Search ..................................... 600/300, 522, 600/523, 525; 607/2, 31, 32, 27, 60; 128/920

[56] References Cited

U.S. PATENT DOCUMENTS 5,693,076 12/1997 Kaemmerer ................................ 607/32
5,713,937 2/1998 Nappholz et al. ........................ 607/27
5,722,999 3/1998 Snell ........................................ 607/32

Primary Examiner—William E. Kamm
Assistant Examiner—Kennedy J. Schaetzle

[57] ABSTRACT

An implantable device programmer includes a variety of features for allowing a clinician to perform an automated and customized follow-up examination of a patient having an implanted cardiac implantable device, the implantable device being of the type which captures and stores various types of diagnostic data for subsequent retrieval and evaluation. A custom protocol feature of the programmer allows the clinician pre-specify and then semi-automatically follow an ordered sequence of protocol steps, each protocol step involving the interrogation of the implantable device and the display by the programmer of associated implantable device data (such as a heart rate histogram, or the results of a ventricular capture test). When the clinician initiates a custom protocol, the programmer automatically retrieves all of the diagnostic data records of the protocol in the protocol order. This automatic retrieval is performed in the background, allowing the clinician to begin viewing the initial diagnostic data records of the protocol while the other items are being retrieved. Via a user interface of the programmer, the clinician can rapidly and efficiently sequence through the data display screens associated with the protocol, to thereby view the various diagnostic data records and/or perform the various diagnostic tests of the protocol.

72 Claims, 9 Drawing Sheets

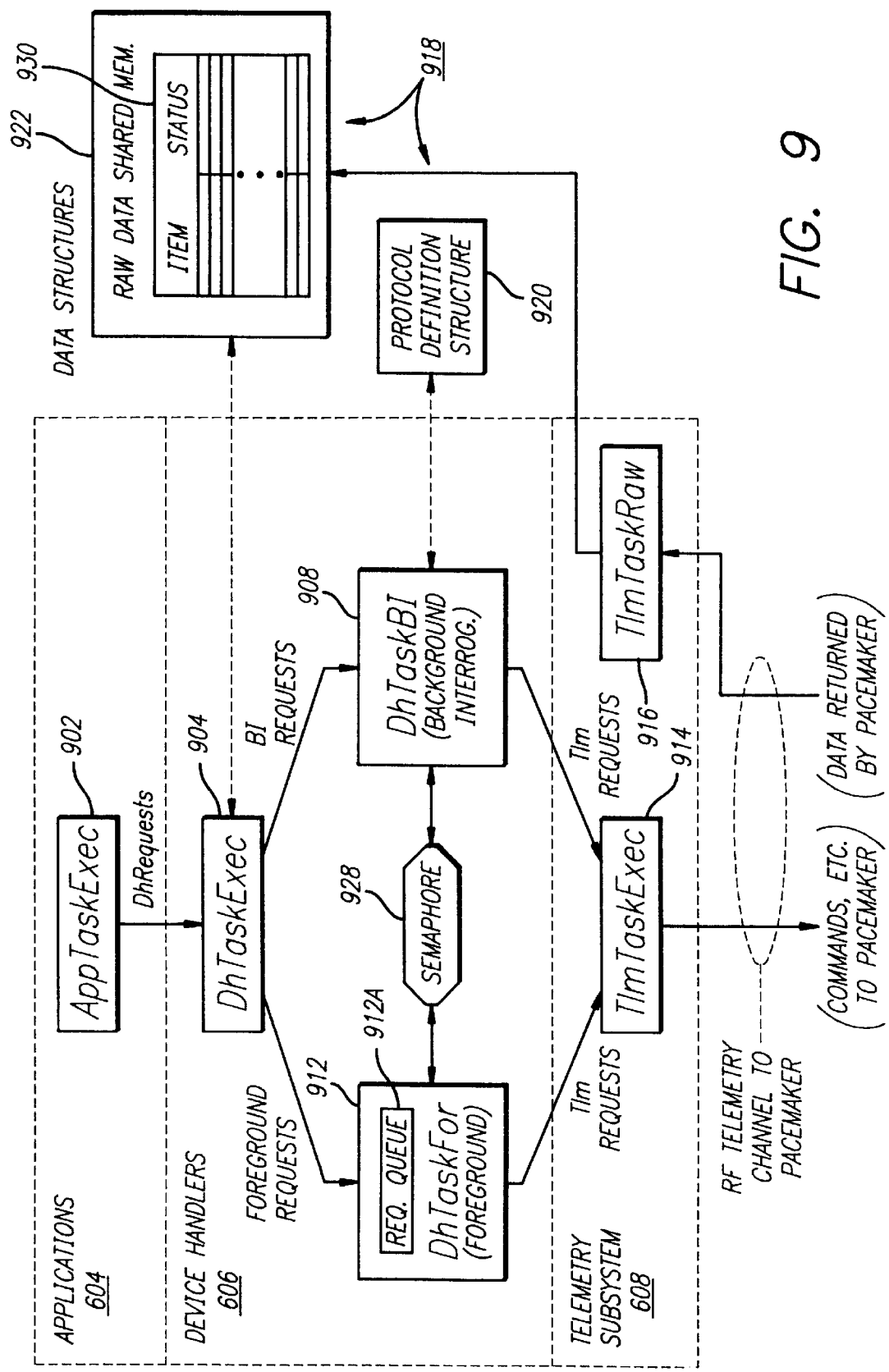

SYSTEM AND METHOD FOR FACILITATING RAPID RETRIEVAL AND EVALUATION OF DIAGNOSTIC DATA STORED BY AN IMPLANTABLE MEDICAL DEVICE

CROSS REFERENCES

This application claims the benefit of U.S. provisional patent application No. 60/015,503, filed May 14, 1996.

Field of the Invention

The present invention relates generally to implantable medical devices, such as implantable cardiac pacemakers, implantable cardioverter/defibrillators (ICD's), heart monitors, or any other medical device that provides therapy or records diagnostic data for subsequent retrieval and display by an external programmer. More particularly, the invention relates to a programmer system, including a user interface thereof, for enabling a physician to rapidly and accurately retrieve, evaluate and process diagnostic data stored by the implantable device, and perform diagnostic procedures in a physician-customizable format.

Background of the Invention

Implantable cardiac implantable devices commonly store a variety of different types of diagnostic data which assist the physician in evaluating both the operation of the patient's heart and the operation of the implanted device. The specific collections or "records" of diagnostic data stored by the implanted device may include, for example, a real-time event record of pacing events, a heart rate histogram (which indicates the distribution of the patient's heart rate), an event histogram (which indicates the distribution of the various pacing events), a sensor-indicated-rate histogram (which indicates a count and range distribution of a sensor-driven pacing rate), and a history of the implantable device's battery voltage. In addition, the implantable device may store one or more event-triggered snapshots of real-time data, such as a snapshot of intracardiac electrogram ("IEGM") data following a detected arrhythmia. In modern implantable devices, the number of these different records of diagnostic data can be quite high—often in the range of 30 or more.

The various records of diagnostic data may be retrieved from the implantable device for display and evaluation using an implantable device programmer, which uses telemetry to communicate with the implanted device. This is typically accomplished during routine follow-up visits of the patient to the clinic, during which time the patient is asked to hold a telemetry wand adjacent to the implanted implantable device. To read out and view a particular record of diagnostic information (e.g., a heart rate histogram), the physician uses a user interface of the programmer to designate the record to be retrieved, and then initiates the retrieval. The programmer, in turn, interrogates the implantable device to cause the implantable device to transmit the selected record, and then receives and displays the selected record (typically in a graphical format) on the screen. The physician may also initiate various types of diagnostic tests using the programmer, such as a ventricular or atrial capture test which determines the minimum pulse voltage needed to effectively stimulate the respective chamber of the heart. The physician may also retrieve, view, and possibly adjust various programmable pacing parameters, such as sensor control parameters that are used to vary the pacing rate according to the output of an activity (or other) sensor.

During the follow-up visit, it is common for the physician (or other clinician) to follow a predetermined sequence of steps or "protocol" to evaluate the patient and the implanted device. The particular protocol will often vary from physician-to-physician and/or from clinic-to-clinic, and may depend upon the medical condition or the type of implanted device of the patient. By way of example, a follow-up protocol may include the ordered steps of (1) retrieving the stimulation, sensing, timing and sensor parameters; (2) retrieving, viewing and printing the atrial and ventricular rate histograms; (3) retrieving and viewing (and optionally printing) the event histogram; (4) conducting ventricular and atrial sense tests and capture tests; (5) contingent upon the results of steps 1–4, retrieving and viewing the R-wave and P-wave histograms; (6) retrieving, viewing and printing the sensor indicated rate histogram; and (7) if appropriate, adjusting various control parameters. During each step of the protocol, the physician typically interviews the patient and records the patient's comments. At the end of the examination, the physician normally prepares a written report, which typically includes various printouts of retrieved diagnostic data records.

One problem with the current follow-up practice is that it tends to be time consuming. For example, assuming that no adjustments are made to the implantable device parameters, it will typically take the physician 20 to 25 minutes to sequence through the steps of the follow-up protocol. This is due in-part to the need for the physician to interactively specify each diagnostic record to be retrieved, and then wait for the programmer to retrieve and display the data record. In addition to affecting the physician's efficiency, this time penalty is often burdensome to the patient, since the patient typically must hold the telemetry wand in place throughout most or all of the procedure.

Another problem with the current practice is that the physician often fails to retrieve and evaluate clinically significant diagnostic data records stored within the implantable device. In fact, it is currently common practice for the physician to retrieve certain diagnostic data records only if the patient is symptomatic. As a result, clinically significant data is frequently overlooked during the diagnostic decision process. One reason for this under-utilization of diagnostic information is the amount of time required, with existing programmers, to retrieve and review each diagnostic record. Another reason, which is related to the storage by newer implantable devices of diagnostic data records not stored by earlier implantable devices, is that it is burdensome for the physician to follow different protocols for different implantable devices.

SUMMARY OF THE INVENTION

The present invention addresses these and other concerns by providing an implantable device programmer which includes a variety of interrelated features for automating and permitting the customization of the follow-up evaluation process. These programmer features significantly reduce the amount of time required for the clinician to perform a follow-up session, while allowing the clinician to focus on communicating with the patient (as opposed to interacting with the programmer) during the session. In the preferred embodiment, the features require no modification to the design of the implantable stimulation device, and can thus be used in the examination of patients with older cardiac implantable devices.

In accordance with one aspect of the invention, the programmer includes a custom protocol feature which allows a clinician to create a custom follow-up protocol to be used during follow-up sessions with patients. The custom protocol is created by selecting from a list of the available diagnostic and testing display screens corresponding to the implantable device or family of implantable devices, and by specifying a default order in which the display screens are to be displayed during follow-up sessions. These display screens correspond to specific diagnostic data records (such as a heart rate histogram or a sensor-indicated-rate histogram) and parametric data items (such as a set of sensor parameters) which may be retrieved and displayed during the follow-up session, and to particular diagnostic tests (such as a ventricular capture test or an atrial sense test) which may be performed during the session.

Thus, by selecting a particular set of display screens to be included in the custom protocol, the clinician specifies the data items (i.e. diagnostic data records and parametric data items) to be retrieved and viewed, and the diagnostic tests to be performed, during the follow-up session. (As described below, the programmer allows the clinician to depart from the custom protocol during the follow-up session to view other data items and/or conduct other diagnostic tests.)

In addition, the clinician can specify, as part of the custom protocol, a set of display screens to be printed, including a print order for the printing of such display screens (which, in one embodiment, may advantageously differ from the viewing order); the clinician can thereby specify the content and format of a custom printed report, which may differ from the sequence of display screens viewed during the follow-up session. With respect to the diagnostic data records of the protocol, the clinician can also pre-specify whether or not the record should automatically be cleared from implantable device memory following retrieval.

Once a custom protocol has been created, the protocol may be saved (using an appropriate file name) in the programmer for subsequent recall and use. Of course, a clinician may create many different custom protocols which may correspond, for example, to different medical conditions, different types of implantable medical devices, and/or to different types of examination sessions (e.g., initial follow-up session, routine follow-up session, initial programming session, etc.). In addition, with clinics that have multiple physicians, different physicians may advantageously create and use their own respective protocols.

To use the custom protocol feature during a follow-up session (or other type of examination session) with a patient, the clinician initially uses the user interface of the programmer to select an appropriate custom protocol. The clinician may alternatively select one of the standard follow-up protocols provided with the programmer. Once a protocol has been selected, and the patient has been instructed to hold the telemetry wand adjacent to the implanted implantable device, the clinician initiates the protocol by selecting (e.g., depressing or clicking on) a "start protocol" button of the graphical user interface.

Thereafter, the programmer automatically retrieves all of the diagnostic data records and parametric data items of the protocol, without requiring any additional input from the clinician, and begins printing the designated reports in the print order of the protocol. The clinician may then step through the set of display screens, in the default viewing order of the protocol, by simply selecting a "CONTINUE PROTOCOL" button 232 of the graphical user interface. (As described below, a "background interrogation" feature of the programmer allows the clinician to begin viewing each individual diagnostic data record and parametric data item in the "foreground" as soon as it has been retrieved, while the programmer continues to transparently retrieve the subsequent data items of the protocol in the background.) This is in contrast to existing programmers, with which the clinician typically must interactively specify each individual diagnostic data record to be viewed and then wait for the record to be retrieved and displayed by the programmer.

In addition, the clinician may at any time "depart" from the protocol to access a display screen that is not part of the protocol, or to jump ahead to a later display screen of the protocol. For example, instead of selecting the "CONTINUE PROTOCOL" button, the clinician may select a menu option which allows an atrial capture test (which may or may not be part of the protocol) to immediately be performed. Upon returning to the protocol, the programmer continues the protocol where the clinician left off, with the exception that the clinician will not be re-shown any display screen viewed by the clinician during the protocol departure.

Similarly, the programmer may also perform some diagnostics in the background and suggest a departure from the physician specified custom protocol. For example, if an incorrect test sequence is initiated by the custom protocol for that particular model number or operating mode, then the programmer may automatically skip the incorrect tests. Additionally, if a potential problem, or other condition, is diagnosed during the background interrogation, the programmer can interrupt the custom protocol and suggest viewing this data first.

As will be readily appreciated by those skilled in the art, the custom protocol feature provides a number of significant advantages over existing programmers and methods of use thereof. One advantage is a significant reduction in the interaction required between the clinician and the programmer to follow a particular protocol. This allows the clinician to focus on interviewing the patient, rather than being concerned with the menu selections needed to view and/or print the various display screens.

Another advantage is a significant reduction in the time required to conduct a follow-up session. This reduction is due in-part to the reduction in the number of menu selections required, and is also due in large part to the background interrogation feature (discussed below) of the programmer, which makes extremely efficient use of the available telemetry bandwidth for retrieving diagnostic data from the implantable device. In fact, when combined with features of the programmer which permit the automation of certain diagnostic tests, it has been found that the time required to complete a typical follow-up protocol can be significantly reduced from about 20–30 minutes to about 3 minutes.

Another advantage of the custom protocol feature is that it helps to ensure that all of the clinically significant information stored by the implantable device will be considered during the follow-up session. For example, for a physician that normally follows a follow-up protocol, the feature helps to ensure that no step of the protocol is accidentally skipped, even if the physician temporarily departs from the protocol. As a result of the time savings and added convenience provided by the custom protocol feature, it is also believed that many physicians will take the time to view more of the diagnostic data records stored by implantable devices.

In accordance with another aspect of the invention, whenever a clinician initiates either a custom or a non-custom (standard) protocol, the programmer uses a background interrogation process to rapidly and transparently retrieve the data items specified within the protocol. In accordance with this feature, the programmer retrieves the diagnostic data records and other data items (such as parameter sets) in the viewing order of the protocol. Thus, for example, if the first record to be viewed as part of a protocol is a heart rate histogram, the programmer will retrieve this diagnostic record first (by appropriately interrogating the implantable device to cause the transmission of the data), and then automatically proceed to the next item of the protocol.

Advantageously, once any given diagnostic data record (or other data item) has been retrieved (i.e., is resident within the memory of the programmer), the clinician can immediately view the record on the screen of the programmer while the programmer continues to interrogate the implantable device in the background to retrieve the other diagnostic data records of the protocol. This ability to immediately view retrieved data items (i.e., diagnostic data records and parametric data items), combined with the automatic ordering of the retrieval to match the protocol, allows the clinician to rapidly progress through the display screens of the protocol, without having to wait longer than necessary for a given display screen to become ready to view.

Moreover, if, during the background interrogation process, the clinician initiates a operation (referred to as a "foreground operation") which requires the use of the telemetry channel, the background interrogation process is temporarily halted to allow the programmer (and clinician) to immediately perform the foreground operation. This situation arises, for example, when the clinician departs from (e.g., jumps ahead in) the protocol to view an item that has not yet been retrieved, or initiates a diagnostic test (which may or may not be part of the protocol) that makes use of the telemetry channel. This feature of the invention is implemented in-part using two device handler software tasks—one in charge of background interrogation and the other in charge of foreground operations—which contend with one another for control of the telemetry channel. To ensure that foreground operations are given priority over background operations without noticeable delay, the two software tasks implement a contention protocol in which the background interrogation task relinquishes control of the telemetry channel within a short time (250 milliseconds in the preferred embodiment) after a foreground operation becomes pending.

The programmer software can selectively be configured by the clinician such that once all of the protocol data items have been retrieved, the programmer proceeds to retrieve any additional data items that were not specified as part of the protocol. (With modern implantable devices, this entire retrieval process takes about 45 seconds.) Thus, for example, if the clinician wishes to view such additional diagnostic records upon completion of the protocol, these records will normally already be resident within programmer memory and ready to view. Upon completion of the follow-up session, the programmer automatically stores all of the data items retrieved during the session (including any items that were not viewed by the clinician) within a log file on the programmers hard disk.

The present invention can thus be used as a therapy management tool to benchmark the patient status at follow-up. More specifically, the system could, during background interrogation, record the initial therapy, perform the diagnostics specified in the physician customized protocol, record the final therapy, and provide a summary of the changes in therapy and alert the clinician to any significant changes.

BRIEF DESCRIPTION OF THE DRAWINGS

These and other features and advantages of the invention will now be described with reference to the drawings of a preferred embodiment, which is intended to illustrate and not to limit the invention, and in which:

FIG. 9 is an architectural drawing of the software components used for performing background and foreground interrogation.

DETAILED DESCRIPTION OF THE INVENTION

In accordance with a preferred embodiment of the invention, an implantable device diagnostic and programming system ("programmer") is provided which includes a variety of features for allowing a clinician to automate and customize follow-up examination sessions with patients. (As used herein, "clinician" refers to any physician, nurse, or other medical professional who participates in the examination of patients.) These features are accessible via an "automated follow-up" menu option of the programmer. One such feature allows the clinician to semi-automatically follow a predefined follow-up protocol (defined within the memory of the programmer), significantly reducing the interaction required between the clinician and programmer during the follow-up session. This predefined protocol can be either a "custom protocol" generated and saved by the clinician using the programmer's user interface, or a "standard protocol" provided with programmer.

Another such feature, referred to as "background interrogation", allows the clinician to view diagnostic data records (e.g., heart rate histograms, event records, etc.) that have been retrieved from the implantable device while other diagnostic data records are being retrieved in the background. This feature is invoked whenever the clinician uses the automated follow-up option to follow a predefined protocol (which may be either a custom or a standard protocol). To maximize the benefit of this feature, the background retrieval of diagnostic data records is performed in an order which corresponds to the viewing order defined within the protocol, to thereby reduce the likelihood that the clinician will have to wait for a particular data item to be retrieved.

To facilitate a complete understanding of the invention, the detailed description is arranged as follows. An overview of the follow-up examination process of a patient having an implanted device is initially provided below under the heading OVERVIEW. The automated follow-up (protocol and background interrogation) features of a preferred programmer are then described under the headings USER INTERFACE, AUTOMATED FOLLOW-UP, BENEFITS OF AUTOMATED FOLLOW-UP, and OTHER FOLLOW-UP RELATED FEATURES, with emphasis on the interactions between the clinician and the programmer. The hardware and software architectures of the programmer are then described under the headings HARDWARE ARCHITECTURE and SOFTWARE ARCHITECTURE AND DATA FLOW. A low level description of the background interrogation feature is then provided under the heading BACKGROUND INTERROGATION, with emphasis on the software components used to implement the feature.

1. OVERVIEW (FIG. 1)

Figure 1:
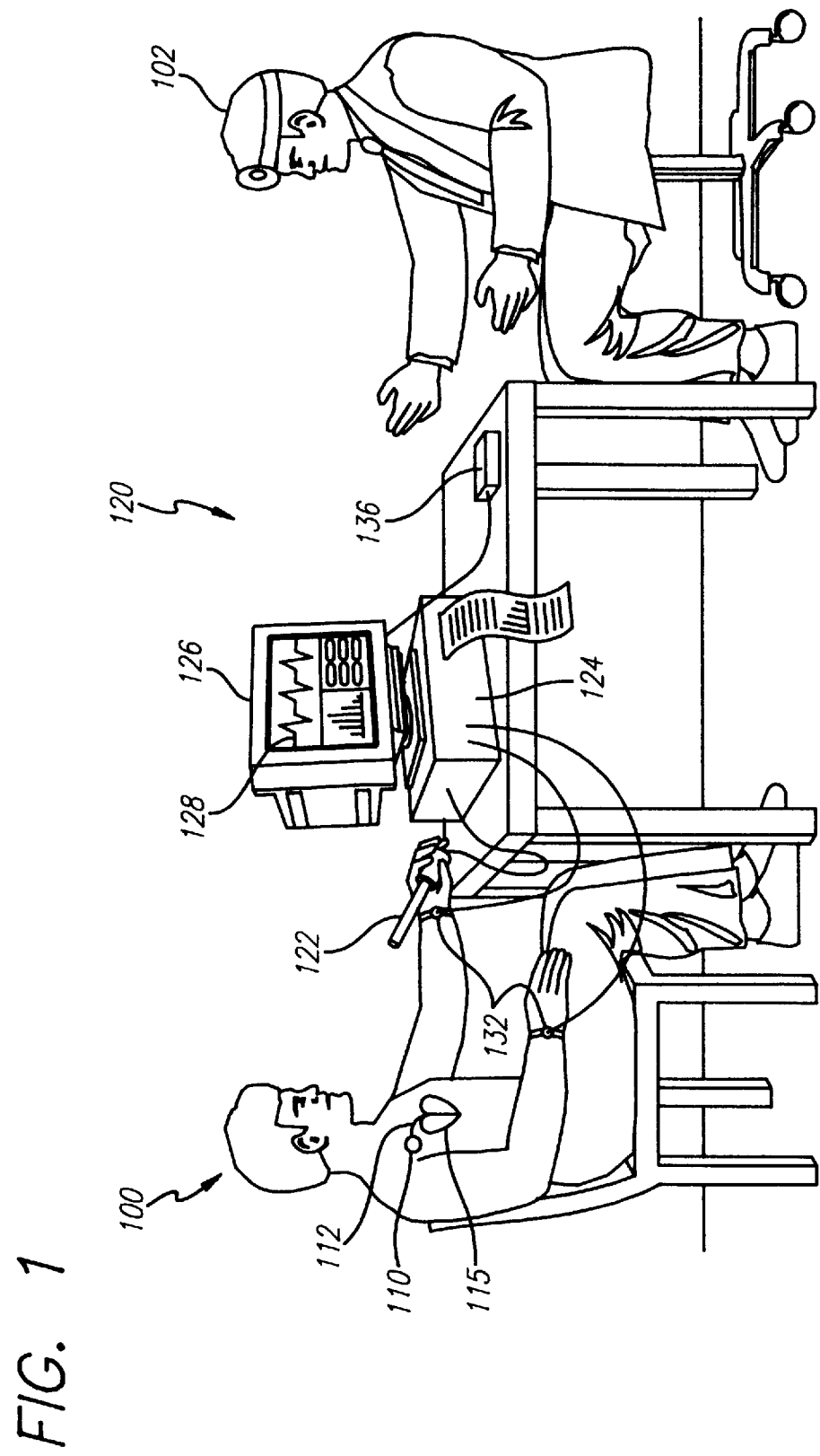
FIG. 1 illustrates a patient in the context of a follow-up session with a clinician using a programmer system in accordance with the invention.

FIG. 1 is a diagram of a patient 100 in the context of a hypothetical follow-up session with a clinician 102, and will be used to provide an overview of the follow-up examination process. The patient has an implantable stimulation device 110. One or more pacing leads 112 extend from the implantable stimulation device 110 into the patient's heart 115. The pacing leads 112 are used to apply electrical pulses to the inner tissue of the heart (typically within the right ventricle and/or the right atrium), and may also be used to sense intrinsic electrical activity within the heart. The implantable stimulation device 110 and/or the leads 112 may also carry one or more sensors (not shown), such as an activity sensor for sensing changes in the patient's level of physical activity.

The implantable stimulation device 110 includes conventional telemetry circuitry (not shown) which permits the exchange of information with an external programmer 120 via a conventional telemetry wand 122. In the preferred embodiment, the programmer 120 includes, for example, a 486 (or Pentium® available from Intel) based computer system 124, and includes a monitor 126 having a touch-sensitive display screen 128. (In one implementation, the display screen 128 and computer system 124 are integrated within a common housing.) The computer system 124 may be provided with an internal printer, as depicted in FIG. 1, and/or may be connected to an external printer (not shown).

During the follow-up session, the patient 100 is asked to hold the telemetry wand 122 near the implanted implantable stimulation device 110 to permit the interrogation of the implantable stimulation device 110, which involves the transmission of telemetric commands to the implantable stimulation device 110. Data transfers between the programmer 120 and the implantable stimulation device 110 are accomplished using a standard interrogation protocol, in which the programmer 120 transmits commands (via the telemetry wand 122) to the implantable stimulation device 110 to cause the implantable device to take specific actions, such as transmit a particular record of diagnostic data.

In addition to the data collected from the implantable stimulation device 110, the programmer receives surface electrocardiograph (ECG) signals from conventional surface electrodes 132, which attach to the skin of the patient 100. The ECG signals are displayed to the clinician 102 on a continuous, real-time basis via the monitor 126, and are used by the programmer 120 to perform tests relating to, for example, atrial and ventricular capture.

As is conventional in the art, the implantable stimulation device 110 stores a variety of different diagnostic data records, including various types of histograms, real-time event records, event counters, and event-triggered snapshots of data. These diagnostic data records are collected by the implantable stimulation device 110 over a period of time, such as between visits of the patient to the clinic, and can be retrieved and displayed to allow the clinician to evaluate the effectiveness of the pacing treatment. The stored diagnostic data records may also include information relating to the operation of the implantable device itself, such as a history of the implantable device's battery voltage. (Accordingly, as used herein, the term "diagnostic data record", or simply "diagnostic record", refers to a collection of data captured or generated by the implanted device over a period of time, which may be retrieved from the implanted device to obtain information about the patient and/or the operation of the implanted device.) The particular diagnostic data records stored by the implantable stimulation device 110 depend upon both the model of the implantable device and its programmed mode of operation.

As is also conventional, the implantable stimulation device 110 stores a variety of parameters (referred to generally as "parametric data") which define the therapy administered by the implantable stimulation device 110, and which can be modified during the follow-up session. These parameters typically include, for example the base rate (i.e., the rate at which pulses are applied to the heart in the absence of intrinsic activity), the AV delay (i.e., the delay between a sensed or paced atrial event and the delivery of a ventricular output pulse), the amplitude and width of pulses applied to the atrium and/or ventricle, and various sensor parameters for defining the control relationship between sensor output and pacing rate. As with the diagnostic data records, the specific program parameters which may be modified depend upon both the model of the implantable device and its mode of operation. Typically, the parameters are retrieved from the implantable device one set at-a-time (such as the set of all sensor parameters), as opposed to being retrieved on a parameter-specific basis.

In the course of a typical follow-up session (using a programmer 120 in accordance with the invention), the clinician uses the programmer to retrieve, view and print various diagnostic data records, and to clear stored diagnostic data records from memory (to permit the subsequent capture of new diagnostic data). The clinician may also retrieve and view the various sets of parameters, as well as information about the implantable device and the patient. In addition, the clinician may use the programmer to initiate various diagnostic tests, such as an atrial capture test or a retrograde conduction test. Based on the test results and the clinician's evaluation of retrieved diagnostic data, the clinician may choose to modify certain parameters or otherwise modify the treatment of the patient.

As described below, the programmer 120 of the preferred embodiment allows the clinician to perform these various follow-up steps either manually (i.e., by interactively selecting each individual item to be displayed and test to be performed), or by using an "automated follow-up" feature which allows the clinician to semi-automatically follow a predefined follow-up protocol.

2. USER INTERFACE (FIG. 2)

Figure 2:
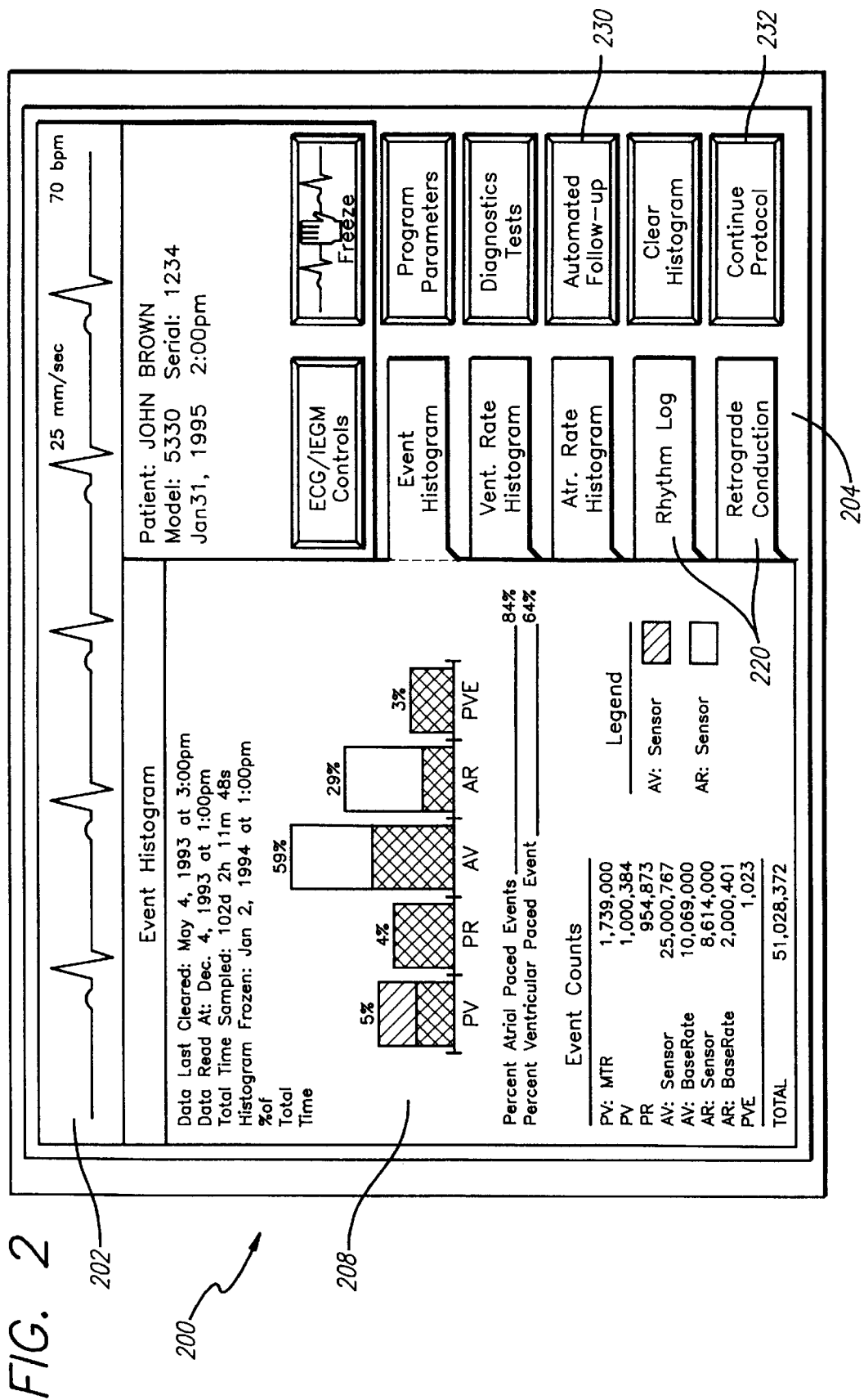
FIG. 2 is an example data display screen of the programmer's user interface.

In the preferred embodiment, the clinician interacts with the programmer 120 and the implantable stimulation device 110 via a graphical user interface of the programmer 120, a representative display screen 200 of which is shown in FIG. 2. The clinician may also use a keyboard (not shown in FIG. 1) to enter remarks and other data.

With reference to the EVENT HISTOGRAM display screen 200 shown in FIG. 2, which is illustrative of the general format of the display screens used for displaying diagnostic and parametric data, the display screen 200 includes three primary sub-screens or "panels:" a real-time data display panel 202, a control panel 204, and a foreground panel 208. The real-time data display panel 202 displays the ECG and IEGM signals (including markers) transmitted, respectively, by the ECG electrodes 132 and the implantable stimulation device 110. (In the FIG. 2 example, only an ECG signal is shown).

The control panel 204 includes various control buttons 220 for allowing the clinician to view other display screens and to initiate other follow-up related events. For example, the clinician can select the "PROGRAM PARAMETERS" button to view the program parameters (via corresponding display screens) stored by the implanted device, or can select a "CLEAR HISTOGRAM" button to clear the displayed histogram from the memory of the implanted device. The control buttons 220 can be selected by pressing corresponding portions of the touch-sensitive screen 128, or by clicking on the buttons using a mouse 136 or other pointing device. The functions performed by some of the buttons are specific to the particular display screen/data item being viewed. (The term "data item" is used herein to refer generally to the diagnostic records, parameters sets and other viewable data sets that can be retrieved from the implanted device and displayed by the programmer.)

The foreground display panel 208 is used to display the data associated with the foreground operation being performed by the clinician. This data may include, for example, a scrollable graph generated as part of an atrial capture test, a retrieved histogram, or a set of parameters. Diagnostic records are displayed within this panel 208 in a preformatted manner, along with associated explanatory text which is within the programmer's display routines. In the example shown in FIG. 2, the diagnostic record (i.e., the EVENT HISTOGRAM data) is displayed in both graphical and tabular form, along with hard coded explanatory text (e.g., the phrase "data last cleared:") of the display screen 200. In general, each diagnostic data record that can be retrieved from the implantable device is displayed using its own respective display screen (such as the EVENT HISTOGRAM display screen shown in FIG. 2). However, some diagnostic records can be viewed in multiple formats via different display screens of the programmer.

The clinician can access the various data display screens either manually (by selecting the corresponding control buttons 220) or semi-automatically (by using the automated follow-up features of the programmer, which can be accessed by selecting the AUTOMATED FOLLOW-UP button 230). Regardless of the method used, when a data display screen is selected (such as the EVENT HISTOGRAM display screen of FIG. 2), the programmer 120 initially checks to see if the corresponding (diagnostic or parametric) data item has already been read from the implanted device into programmer memory. If the data item has already been retrieved (e.g., by background interrogation), it is immediately displayed via the display screen. If the data item has not been retrieved, the programmer begins retrieving the data item (or finishes retrieving the data item if retrieval has already been initiated), and then displays the data item via the display screen.

In addition to the display screens used for the display of diagnostic and parametric data items, the user interface includes display screens and controls which correspond to other types of tasks, including protocol generation (FIG. 4), file management, and diagnostic tests.

3. AUTOMATED FOLLOW-UP (FIGS. 2–4)

As indicated above, one of the automated follow-up features of the programmer 120 involves the use of a pre-specified examination protocol, which may be either a custom protocol (previously specified by the clinician or another user) or a standard (non-custom) protocol provided with the programmer 120. To access this feature, the clinician initially selects an AUTOMATED FOLLOW-UP button 230 (shown in FIG. 2); the clinician is then presented with various controls and display screens which allow the clinician to, for example, define a new protocol, view a list 302 of existing protocols of a particular clinician (FIG. 3), display and edit the steps of a protocol (FIG. 4), and start a selected protocol.

Figure 3:
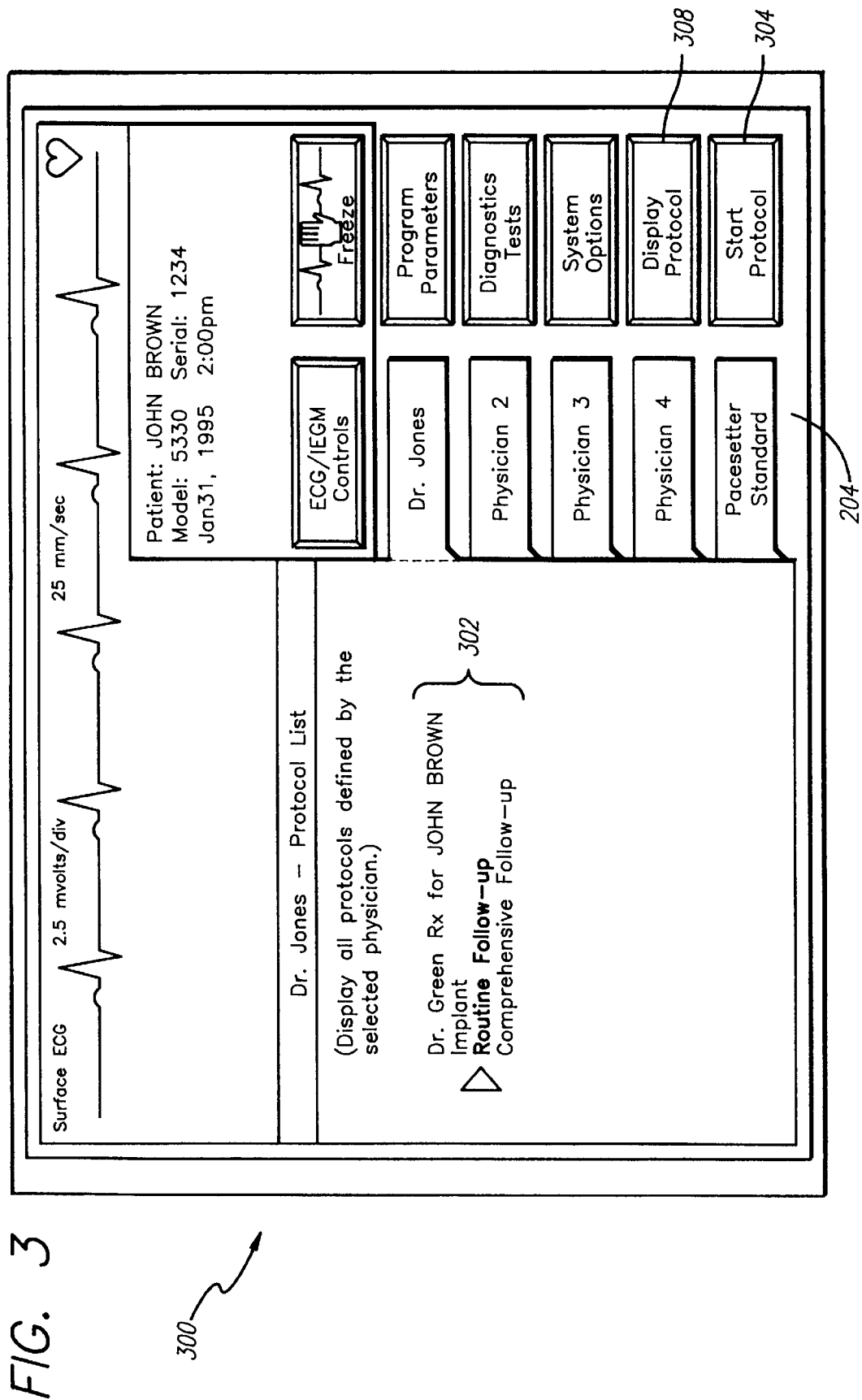
FIG. 3 is a programmer display screen which may be used to select between existing follow-up protocols.

FIG. 3 illustrates a protocol display screen which displays the predefined protocols of a particular clinician. In this example, the clinician (Dr. Jones) has four predefined protocols, each of which is stored as a respective protocol definition file on the Programmer's hard disk. In general, each protocol corresponds to a particular family of implantable device, which may be specified by the clinician prior to defining the protocol. Of course, any suitable naming convention and grouping method can be used for organizing the protocol definition files for display via the user interface. Using either the touch screen 128 or the mouse 136, the clinician can select any one of the displayed protocols. (In the example shown in FIG. 3, the "Routine Follow-up" protocol is selected.) The clinician can then use the "START PROTOCOL" button 304 to start the protocol (i.e., to begin the interrogation process), or use the "DISPLAY PROTOCOL" button 308 to display the steps of the protocol (as shown in FIG. 4).

Figure 4:
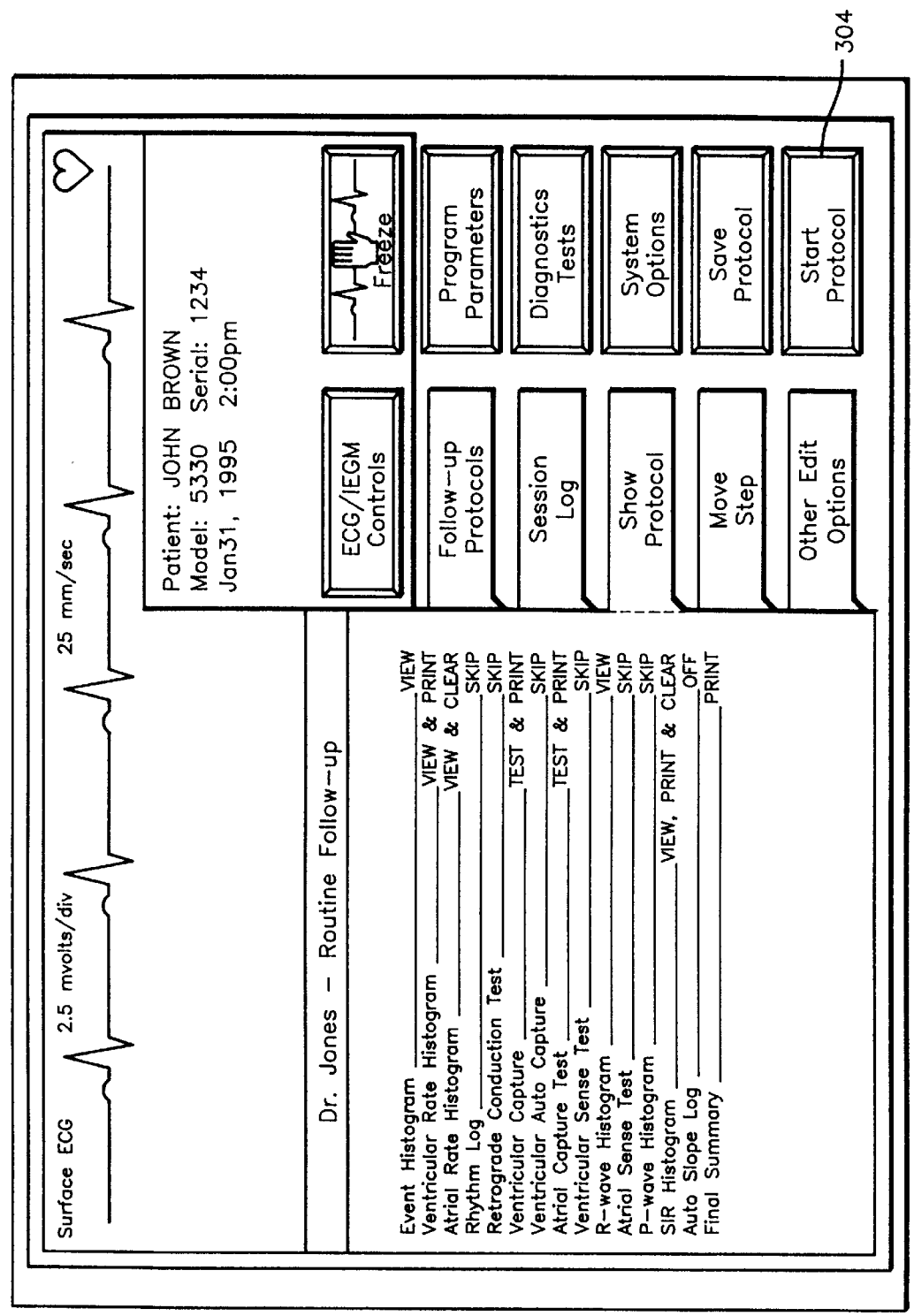
FIG. 4 is a protocol definition display screen of the programmer's user interface.

FIG. 4 illustrates a protocol definition screen, including an example follow-up protocol, in accordance with one embodiment of the invention. From this display screen, the clinician can view the steps of the protocol, modify the protocol (using the MOVE STEP and OTHER EDIT OPTIONS BUTTONS, as described below), and/or start the protocol. The clinician can also generate new custom protocols by, for example, modifying the steps of the displayed protocol and then saving the modified protocol under a new filename.

As illustrated by the example protocol displayed in FIG. 4, each protocol consists generally of an ordered list of protocol steps, with each step consisting of an identifier of a display screen (e.g., "EVENT HISTOGRAM" and "VENTRICULAR RATE HISTOGRAM") along with an action to be performed (e.g., VIEW or PRINT) with respect to the display screen. ("SKIP" indicates that no action will be performed. In other embodiments, only the protocol steps which include an action other than SKIP are displayed in the protocol definition screen.) In this example, the first automated action to be performed will be the retrieval and display of the EVENT HISTOGRAM, and the second automated action will be the retrieval, display and printing of the VENTRICULAR RATE HISTOGRAM.

In another preferred embodiment, the programmer 120 allows the clinician to separately specify an ordered list of the display screens to be printed. The clinician can thereby specify a print order which differs from the protocol's viewing order. This feature allows the clinician to flexibly specify the order of the printed display screens within a custom follow-up report. For example, the clinician designate the FINAL SUMMARY display screen (which summarizes the follow-up session) as the first page of the printed report, even though the display screen was viewed at the end of the follow-up session.

Table 1, which is attached at the end of this disclosure, lists a master set of the protocol steps (each corresponding to a respective display screen) that can be included in a custom protocol for a family of implantable devices. Listed to the right of each protocol step are the options that can be specified by the clinician for each protocol step. Using edit buttons such as the MOVE STEP and SAVE PROTOCOL buttons of FIG. 4 (and other edit buttons that can be accessed by selecting the OTHER EDIT OPTIONS button), the clinician can create, modify and save follow-up protocols which include various combinations of these protocol steps. (Options designated with a star symbol are the default options which are used if no option is specified by the clinician.) During the protocol generation process, only those steps that are supported by the pre-specified family of implanted device are displayed to the clinician. The protocol steps and options listed in Table 1 represent one preferred implementation of the automated follow-up software, and are not intended as a comprehensive list of the types of actions that can be performed using the custom protocol feature.

Once a follow-up protocol has been initiated (using the "START PROTOCOL" button 304), the programmer 120 begins to retrieve the diagnostic and parametric data items of the protocol (using background interrogation, as described below) from the implanted device. As the data items are retrieved, the clinician can semi-automatically sequence through the -various display screens of the protocol (to view the corresponding diagnostic and parametric data items and to conduct the corresponding tests) by simply selecting the "CONTINUE PROTOCOL" button 232 (FIG. 2), which causes the next display screen of the protocol to be displayed. (In other embodiments, this button may, for example, be in the form of a hand-held push button which attaches to the programmer 120 by a cord, as commonly used with slide projectors.)

In addition, the clinician can depart from the protocol (to, for example, view a non-protocol diagnostic record, or temporarily jump ahead in the protocol) at any time, and then return to the protocol by selecting the "CONTINUE PROTOCOL" button 232. Advantageously, selection of the "CONTINUE PROTOCOL" button 232 will not cause any display screen to be re-displayed. Thus, for example, if the clinician jumps ahead in the protocol to view the event histogram, the programmer will subsequently skip over the event histogram screen when the clinician continues the protocol. As the clinician views the protocol display screens, the designated print screens are automatically printed in the background, in the order specified within the protocol.

If, during a follow-up session, a protocol is used which includes steps that are not supported by the implanted device, the programmer 120 automatically skips over the unsupported steps.

As indicated above, whenever the clinician follows a predefined protocol, the programmer 120 uses a background interrogation process to automatically retrieve the diagnostic and parametric data items corresponding to the protocol. This feature advantageously enables the clinician to view some protocol items (e.g., a heart rate histogram, or a list of sensor parameters) while other protocol items are being retrieved by the programmer 120 in the background (transparently to the clinician). This in-turn reduces or eliminates the need for the clinician to wait for each data item to be retrieved—a process which typically takes a few seconds or more per retrievable data item. To maximize the benefit of this feature, the background interrogation is carried out in an order which corresponds to the viewing order specified within the protocol. Thus, for example, if the first display screen of the protocol is the event histogram screen, the programmer 120 retrieves the event histogram data first, and then automatically proceeds to retrieve the next protocol item.

Whenever, during the background interrogation process, the clinician initiates an operation (referred to as a "foreground operation") which requires the use of the telemetry channel, the background interrogation process is temporarily halted to allow the programmer (and clinician) to immediately perform the foreground operation. (The term "telemetry channel" refers generally to the hardware and software/firmware components used to transfer information between the programmer 120 and the implanted device.) This situation arises, for example, when the clinician departs from (e.g., jumps ahead in) the protocol to view an item that has not yet been retrieved, or initiates a diagnostic test (which may or may not be part of the protocol) that makes use of the telemetry channel. This feature ensures that the step currently being performed by the clinician (i.e., the foreground step) is given the highest data transfer priority, so that the clinician need not wait unnecessarily for the retrieval of data items unrelated to the follow-up step being performed. As described below, this feature of the invention is implemented in-part using two device handler software tasks—one in charge of background interrogation and the other in charge of foreground telemetry operations—which contend with one another for control of the telemetry channel. Once the foreground telemetry operation has been completed, the programmer 120 automatically resumes the background interrogation process to retrieve the data items corresponding to the remaining protocol steps.

The programmer software can advantageously be configured by the user such that, once all protocol data items have been retrieved, the programmer 120 automatically retrieves all other diagnostic and parametric data items (in the background) stored by the implanted device; this advantageously allows the clinician to view non-protocol data items (e.g., at the end of the automated session) without having to wait for interrogation and data retrieval. When this option is selected, all of the retrievable data items stored by the implanted device reside within the programmer's memory at the end of the background interrogation process.

Similarly, the programmer can initiates diagnostic tests (which may or may not be part of the protocol) and subsequently recommend a departure from the protocol to view an item, so that the clinician need not wait unnecessarily for the retrieval of all the data items. As mentioned above, if a potential problem is diagnosed (e.g., an inappropriate lead impedance, loss of sensing, or loss of capture, etc.) during the background interrogation, the programmer can interrupt the custom protocol and suggest viewing this data first. Other conditions (such as, a low battery voltage, or other indicator of the device reaching it's recommended replacement time) may also be detected by the programmer which, in turn, could interrupt the custom protocol to alert the clinician of the unusual condition detected.

In the preferred embodiment, the process of retrieving all of the implantable device data by background interrogation typically takes about 45 seconds, assuming the background interrogation sequence is not interrupted.) The programmer automatically stores this data in a session log file (on the programmer's hard disk) for subsequent recall and use; thus, even if the clinician does not view all of the available diagnostic data during the follow-up session, the data can be viewed at a later time (e.g., during a subsequent patient visit).

While it is contemplated that the background interrogation feature will be most beneficial when used in conjunction with an automated follow-up protocol, it should be noted that the feature can also be used when no protocol is selected. For example, in one embodiment of the programmer 120, background interrogation is used to retrieve all of the implantable device data (in a default order) whenever the clinician performs an initial interrogation of the implanted device.

Advantageously, the custom protocol and background interrogation features of the programmer 120 do not require any modification to the hardware or firmware of existing implantable devices. Thus, these automated follow-up features can be used in the examination of patients with a wide range of preexisting implantable devices. These features can also be used to facilitate data retrieval and analysis with other types of implantable devices, such as defibrillators, drug pumps, and neural stimulators.

The present invention can also be used as a therapy management tool to benchmark the patient status at follow-up. More specifically, the system could, during background interrogation, record the initial therapy (i.e., the pre-follow-up programmed settings, rhythm status, etc.), perform the diagnostics specified in the physician customized protocol, record the final therapy (i.e., the post-follow-up programmed settings, rhythm status, etc.), and provide a summary of the changes in therapy and alert the clinician to any significant changes. Such benchmarking of the patient's status and therapy permits modification of both pharmacological therapy and device therapy. The benchmarking data set can then be stored in the pacemaker, in the programmer, or printed to hard copy. As such, the present invention aids the clinician in identifying which component of the therapy is responsible for any changes in patient symptoms.

4. BENEFITS OF AUTOMATED FOLLOW-UP FEATURES

As will be readily appreciated by those skilled in the art, the above-described automated follow-up features provide a number of significant advantages over existing programmers and methods of use thereof. One advantage is a significant reduction in the interaction required between the clinician 102 and the programmer 120 to follow a particular protocol. This allows the clinician to focus on interviewing the patient 100, rather than being concerned with the menu selections needed to initiate the various diagnostic tests and to retrieve, view and print the various diagnostic data records.

Another advantage is a significant reduction in the time required to conduct a follow-up session. This reduction in time is the result of both (1) the reduction in the number of menu selections required on the part of the clinician, and (2) the data retrieval efficiency which results from the background-interrogation-related features of the programmer. In initial tests, it has been found that a follow-up protocol which normally takes 20–30 minutes when performed manually can be performed in roughly three minutes when the automated follow-up option is used.

In addition to the foregoing efficiency-related advantages, the automated follow-up features help to ensure that all of the clinically significant information stored by the implantable device will be considered during the follow-up session. For example, for a physician that normally follows a follow-up protocol (manually), the feature will help to ensure that no step of the protocol is accidentally skipped, even if the physician temporarily departs from the protocol. Furthermore, as a result of the time savings and added convenience provided by the automated follow-up feature, it is believed that many physicians will take the time to view more of the diagnostic data records stored by implantable devices.

5. OTHER FOLLOW-UP RELATED FEATURES

Briefly, in accordance with one such feature, the programmer 120 includes software routines for stepping through an implantable device test sequence (e.g., a real-time segment of ECG, IEGM and/or marker data) and automatically identifying significant events or transitions (such as the loss of atrial or ventricular capture, substantial heart rate changes, etc.). This feature greatly reduces the amount of time which it takes a physician to evaluate implantable device performance, since the physician is not required to scroll through an entire test sequence to determine the point where a significant test event has occurred.

According to another feature, the programmer 120 includes routines for automatically suggesting implantable device parameter modifications based upon (i) the results of the automatic test sequence analysis and (ii) patient history trends stored within the implantable device. In accordance with another feature, the programmer 120 includes routines for allowing the clinician to interactively modify parameters "on the fly", and evaluate the results of such modifications immediately (i.e., in real time).

6. HARDWARE ARCHITECTURE (FIG. 5)

The hardware architecture of the programmer 120 will now be described with reference to FIG. 5. The software architecture will then be described, with emphasis on the components used for the retrieval of data from the implanted device.

Figure 5:
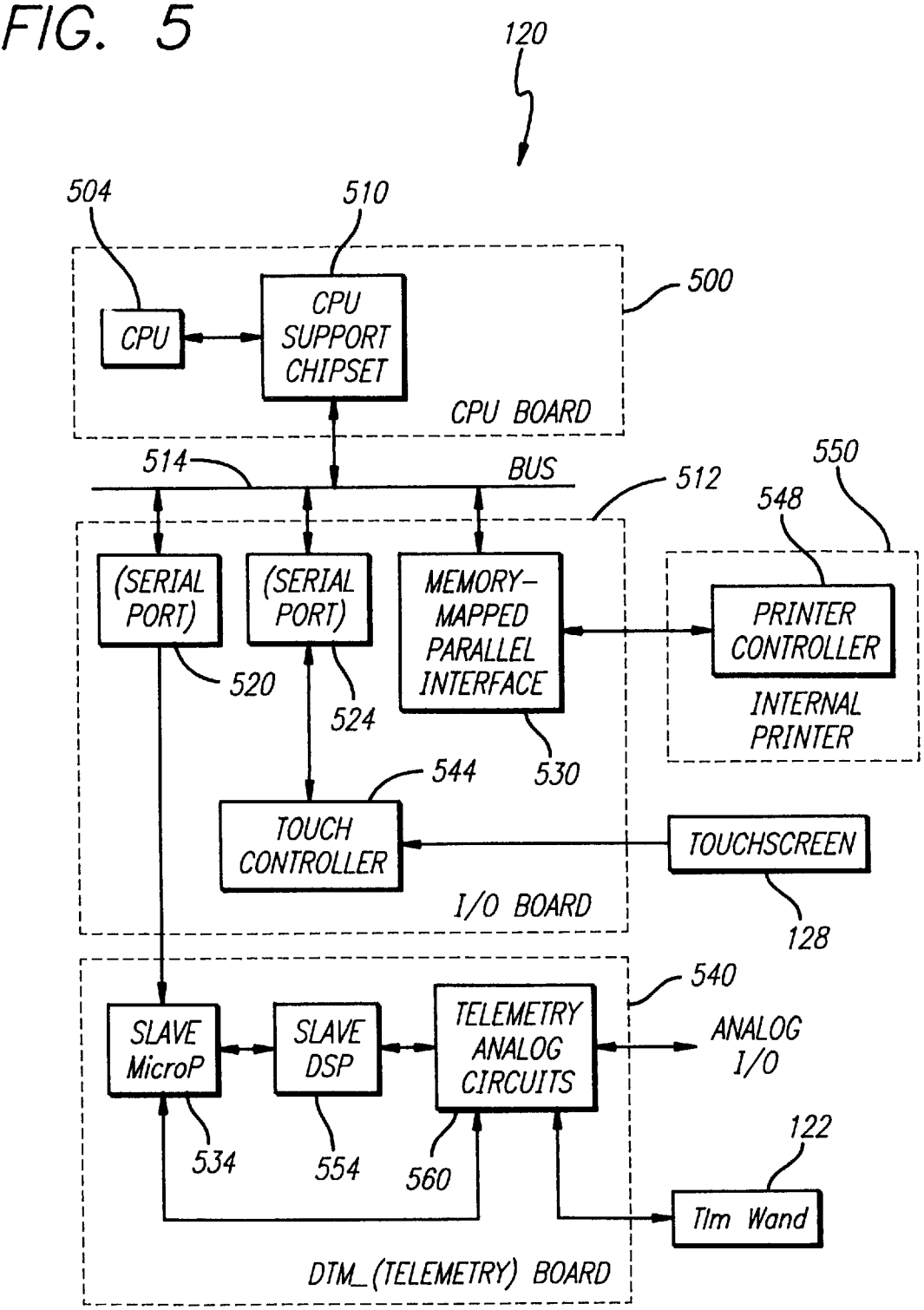
FIG. 5 is an architectural diagram of the primary hardware components of the programmer.

FIG. 5 is an overall system block diagram showing the main internal components of the implantable device programmer 120. As shown in FIG. 5, the programmer 120 includes a central processing unit (CPU) board 500 which includes a CPU 504, such as a 486 based CPU or higher. The CPU 504 communicates with a CPU chip set 510 which may, for example, include buffers, interface circuitry, random access memory (RAM), etc. In one embodiment, at least 16 megabytes of RAM are included in the CPU support chip set 510 for use by the CPU 504.

The CPU board 500 communicates with an input/output (I/O) board 512 via a bus 514, with information being passed between the CPU 504 and the bus 514 via the chip set 510. The bus 514 communicates with serial port interfaces 520 and 524, and a memory-mapped parallel interface 530. Each of the interfaces 520, 524, 530 acts as an interface between a peripheral unit and the CPU board 500. The serial port interface 520 communicates with a slave microprocessor 534 within a telemetry hardware board 540.

The serial port interface 524 communicates with a touch controller 544 on the I/O board 512, which receives inputs from the touch screen 128. In one embodiment, the touch screen 128 is integrally formed with the main chassis 124 of the programmer 120 (not shown in FIG. 1). The memory-mapped parallel interface 530 acts as an interface between the CPU board 500 and a printer controller 548 within an internal printer 550. As illustrated in FIG. 1, the internal printer 550 is preferably integrally formed with the chassis of the programmer 120, although an external printer could alternatively be used.

The telemetry hardware board 540 includes the slave microprocessor 534, as well as a slave digital signal processor (DSP) 554 and telemetry analog circuitry 560. The microprocessor 534 communicates bidirectionally with the slave DSP 554, as well as with the telemetry analog circuitry 560. In addition, the slave DSP 554 communicates bidirectionally with the telemetry analog circuitry 560. The telemetry analog circuitry 560 transmits and receives telemetry signals via the telemetry wand 122.

In one preferred embodiment, the programmer 120 is provided with a modem (not shown) which communicates with a hospital network. Via this modem, the clinician can readily view and/or update patient status information (e.g., transcribed medical reports, images of chest X-rays and ultrasound scans, follow-up session files from previous follow-up visits, etc.) available on the network.

In operation, the CPU 504 serves as a main control processor within the programmer 120. All other processors (including the printer controller 548, the touch controller 544, the DSP 554 and the slave microprocessor 534) act as slaves to the CPU 504. Inputs are provided to the CPU 504 from, the touch screen 128, the telemetry wand 122 (via the slave microprocessor 534), the mouse 136 and an external keyboard (not shown in FIG. 5). In addition, conventional hardware inputs, such as a system clock, are provided to the CPU 504. Furthermore, disk drive inputs from a CD-ROM, hard disk, floppy disk, etc. (not shown in FIG. 5) are provided to the CPU 504. Surface ECG information (not shown in FIG. 5) is also provided to the CPU 504.

The CPU 504 processes the information received via these inputs, and outputs instructions and data to each of the peripheral controllers 548, 544, 534 via the chip set 510, the bus 514, and the I/O board 512. For example, the touch-screen controller 544 may transmit signals to the CPU 504 indicating that the clinician has touched the part of the touchscreen 128 which corresponds to a CLEAR HISTOGRAM button (FIG. 2) of the user interface. The CPU processes this input and in-turn instructs the slave microcontroller 534 to initiate transmission of a command from the telemetry wand 122 to clear a particular histogram from implantable device memory.

The slave microprocessor 534 acts as a control processor of the telemetry hardware board 540. In a preferred embodiment, the slave microprocessor 534 controls the DSP 554 by sending the DSP 554 commands and data. The slave microprocessor 534 also can reset the DSP 554 to regain control of the DSP 554 in the event that the DSP 554 fails to respond properly. The program which is executed within the DSP 554 is preferably downloaded to the DSP 554 from the slave microprocessor 534. In like manner, the slave microprocessor 534 is monitored by the CPU 504, and the CPU 504 can reset the slave microprocessor 534 in the event that the code executing within the slave microprocessor 534 fails to operate properly. The code executed by the slave microprocessor 534 is downloaded to the microprocessor 534 from the CPU 504.

More specifically, the slave microprocessor 534 receives serial commands and data from the CPU 504, telemetry data output from the DSP 554, and signals from the analog circuitry 560. The slave microprocessor 534 processes commands from the CPU 504 and responds to these commands in accordance with requests issued by the CPU 504. The slave microprocessor 534 also monitors the DSP 554 for correct operation, and reloads the DSP program upon a reset condition.

The DSP 554 manages a telemetry protocol at the telemetry frame level, and performs a variety of standard signal processing functions such as filtering IEGM received from the implantable stimulation device 110 and ECG data received from the surface electrodes 132. The touch controller 544 (also referred to hereinafter as the "touch panel processor") serves as a decoder for the touch screen 128. When a user presses a point on the touch screen 128, this information is decoded by the touch panel processor 544 and sent to the CPU 504 via the serial interface 524. The printer controller 548 controls the operation of the internal printer hardware in response to instructions from the CPU 504. The telemetry wand 122 transmits and receives information to and from the implantable stimulation device 110 via a conventional wireless communications link.

7. SOFTWARE ARCHITECTURE AND DATA FLOW (FIGS. 6–8)

Figure 6:
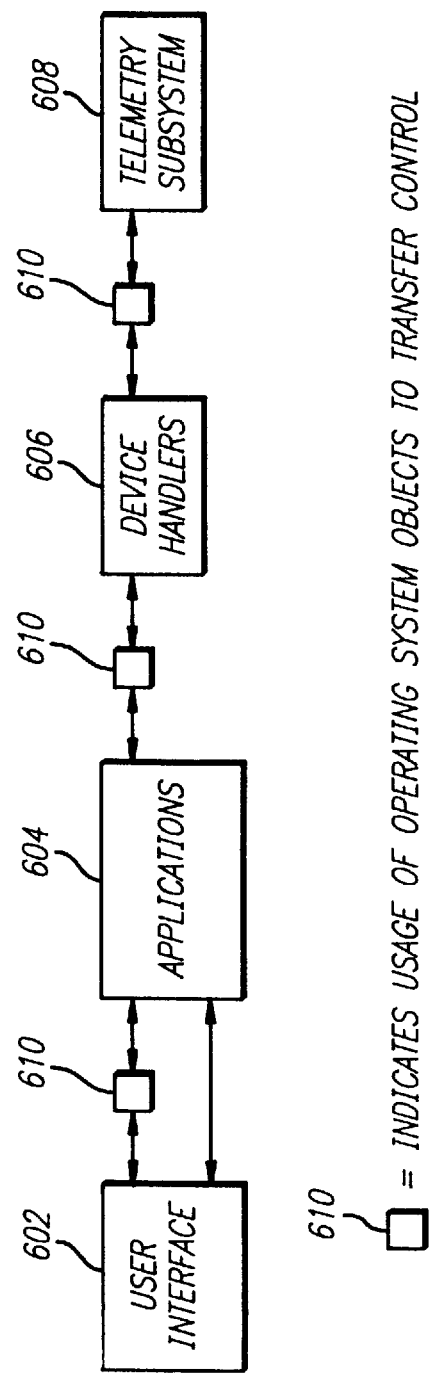
FIG. 6 is a high level drawing illustrating the hierarchy of software components of the programmer.

FIG. 6 illustrates the general hierarchy of software components within the programmer 120. The software components include the user interface 602, applications 604 (also referred to as the "applications subsystem"), device handlers 606, and telemetry software 608. These components run under the control of a real-time multi-tasking operating system, which, in the preferred embodiment, is the VxWorks™ operating system available from Wind River Systems, Alameda, Calif. As illustrated in FIG. 6, the user interface 602, applications 604, device handlers 606, and telemetry components 608 pass information using operating system objects 610. In addition, the applications pass certain information directly to the user interface, without the use of operating system objects.

The user interface 602 receives input from the user through the touch screen 128, mouse 136, keyboard, and other buttons (not shown) of the programmer 120, and passes the information to the applications subsystem 604 as necessary. The user interface 602 also includes facilities for allowing the user to store and retrieve information to/from disk. In addition, in response to calls from the applications subsystem 604, the user interface 602 outputs data to the user via the touch screen 128 (using display screens), the printer 550 and the speaker (not shown).

The applications subsystem 604 is generally responsible for translating user requests into requests for device handler operations, and is responsible for formatting screen and printer output. In addition, during automated follow-up, the applications subsystem is responsible for translating follow-up protocols (specified by protocol definition files) and user input into requests (to the device handlers) for data items. The applications subsystem includes eight discrete tasks for performing different application-level functions. For example, the task AppTaskDisp performs the function of converting raw implantable device image data into a "standard object" form displayable by the user interface 602. Each task utilizes a respective input queue to receive messages, and remains in an inactive state when no message is pending in its respective queue.

The device handlers 606 (also referred to as the "device handler subsystem") are responsible for all implantable device-specific functions, such as interrogation, programming, retrieval of diagnostic and parametric data, and processing of ECG and IEGM data. The device handlers 606 receive requests from the application subsystem (such as a request to retrieve an event histogram), and, as necessary, use the telemetry subsystem 608 to communicate with the implantable stimulation device 110. The device handlers 606 are generally divided into two separate subsystems (shown in FIG. 8)—a wave device handler 606A and a pacer device handler 606B. The wave device handler 606A handles incoming (real-time) ECG, IEGM and marker data. The pacer device handler 606B handles all other implantable device transactions, including interrogation, diagnostic data retrieval, and parameter retrieval/programming.

The telemetry subsystem 608 consists generally of a "host" subsystem (not shown) with runs on the main CPU 504, and "slave" subsystem (not shown) which runs on the slave microprocessor 534 of the telemetry board 540. The host and slave subsystems communicate via the serial interface provided by the serial port interface 520 (FIG. 5). The slave subsystem processes commands from the host, and is responsible for communication with the implantable stimulation device 110. The slave subsystem is also responsible for synchronizing ECG, IEGM and marker data before passing such data to the host subsystem.

Figure 7:
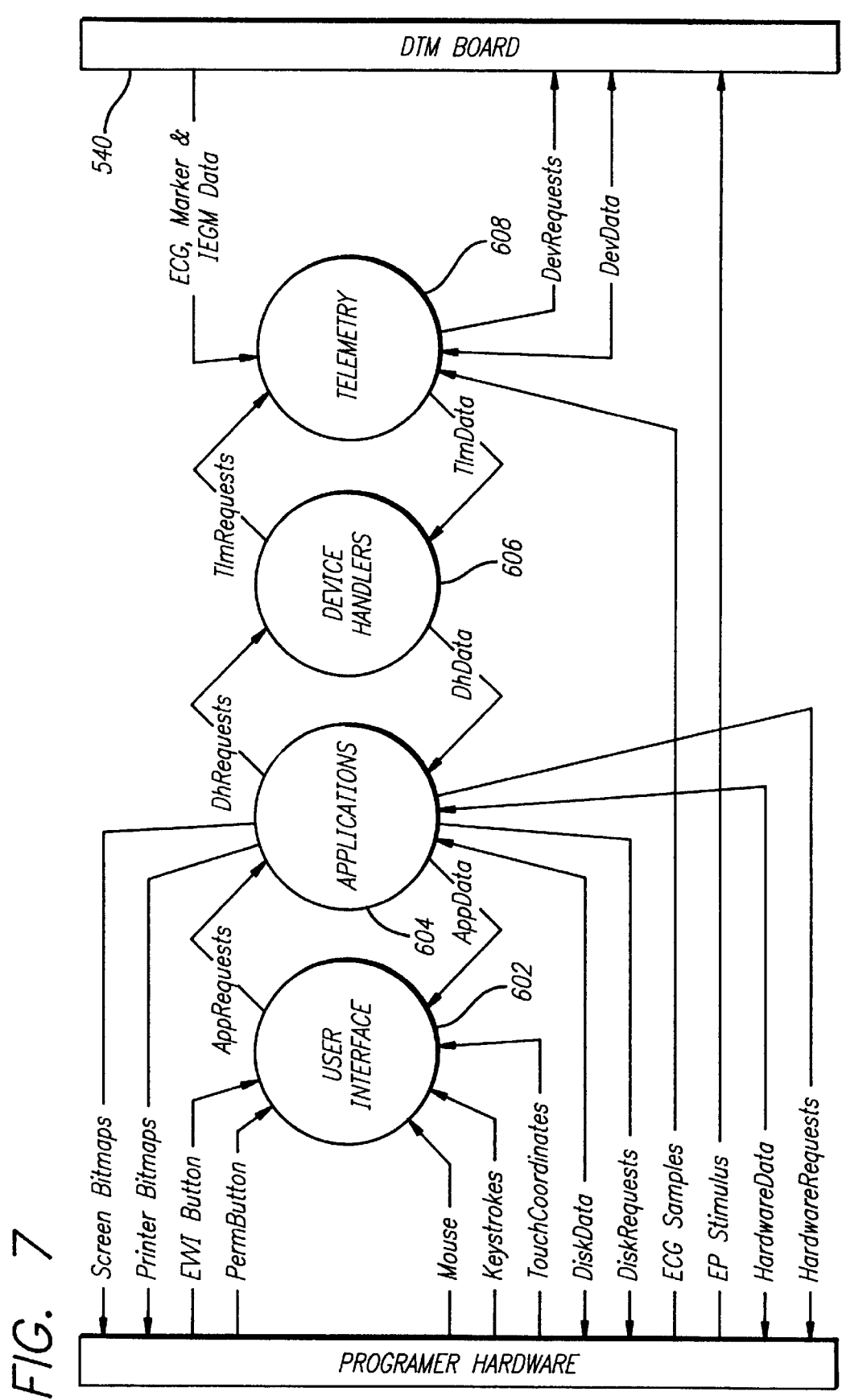
FIG. 7 is a flow diagram illustrating the flow of commands and data between the software and hardware components of the programmer.

FIG. 7 is a flow diagram which illustrates the general flow of information between the software and hardware components of the system. As illustrated, the applications 604 pass device handler requests (DhRequests) to the device handlers 606, which respond by returning requested data (DhData). In the context of automated follow-up, these requests generally include requests for specific diagnostic and parametric data items. For example, the application subsystem 604 may send a DhRequest for an R-wave histogram, which may be followed by a DhRequest for an SIR histogram. (As described below, the DhRequests that are performed by background interrogation are actually in the form of entries in a protocol definition data structure which is generated by the application subsystem 604.)

These DhRequests for data items are effectively subdivided into requests (shown as TlmRequests in FIG. 7) for smaller units of information, and these subdivided requests are passed to the telemetry subsystem 608. Thus, for example, a DhRequest for an event histogram will be transformed by the device handlers 606 into several TlmRequests for sub-packets of the event histogram data. The TlmRequests are normally executed by the telemetry subsystem to completion (i.e., without interruption). However, the device handlers can effectively jump ahead to a subsequent DhRequest (by passing the TlmRequests to the telemetry subsystem 608 out of order) before a current DhRequest has been completed; this advantageously allows the retrieval of a given protocol item to be rapidly interrupted when, for example, the clinician departs from the protocol sequence, or reaches a diagnostic test of the follow-up protocol (as described below).

Figure 8:
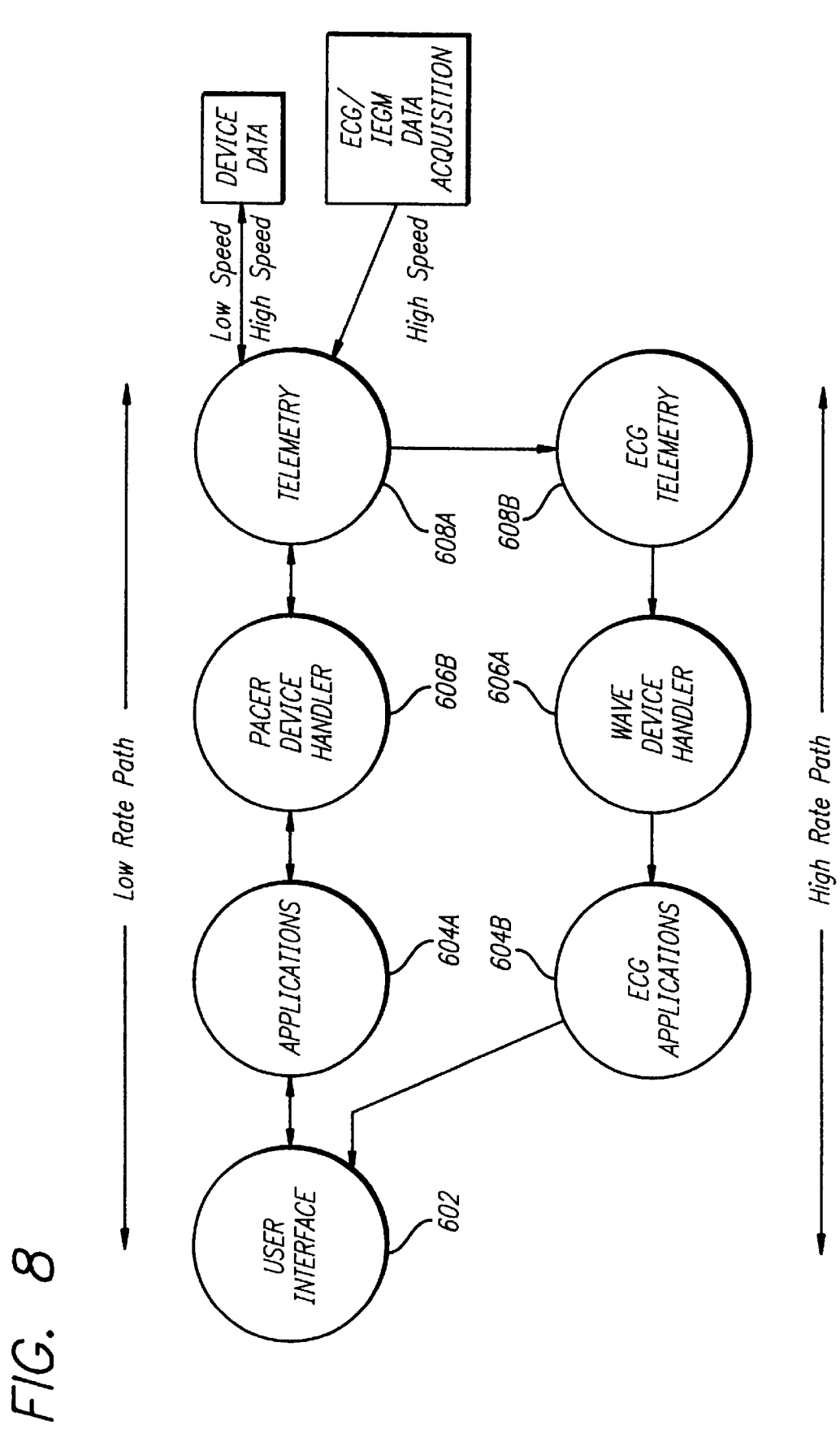
FIG. 8 is a flow diagram showing flow paths taken for different types of information.

As illustrated in FIG. 8, information flows between the software components along two major paths—a "low rate" path and a "high rate" path. The low rate path is used for the transfer of user and protocol commands (e.g., data retrieval requests), and responses to such commands. The high rate path is used for the transfer of real-time ECG, IEGM and marker data. The telemetry interface is implemented such that when the low rate path is inactive, the entire telemetry bandwidth is allocated to the high rate path (i.e., to the transfer of ECG, IEGM and marker data). This allows for the transmission of two IEGM channels with markers.

When the low rate path is active, the low rate path may be allocated either (i) 25% of the available telemetry bandwidth ("low speed mode"), which leaves enough telemetry bandwidth for one IEGM channel, or (ii) the entire telemetry bandwidth ("high speed mode.") The high speed mode is used during background interrogation to reduce the amount of time required for all of the implantable device's data to be read into programmer memory. Thus, for example, when a follow-up protocol is started, the IEGM/ECG display is automatically turned off while the programmer retrieves the protocol items in the background. The programmer 120 may also be configured to use the high speed mode when responding to various types of user commands.

8. BACKGROUND INTERROGATION (FIG. 9)

FIG. 9 illustrates the primary software components that are used for background and foreground interrogation/data retrieval, and will be used to describe the background interrogation process in further detail. In FIG. 9, "BI" stands for "background interrogation", "Dh" stands for "device handler", and "Tlm" stands for "telemetry." In addition, solid arrows designate the flow of requests and responses to requests, and dashed arrows designate accesses to programmer memory structures.

With reference to FIG. 9, the primary executable tasks that are used for background (and foreground) interrogation/data retrieval are: an application executive task (AppTaskExec) 902, a device handler executive task (DhTaskExec) 904, a background interrogation device handler task (DhTaskBI) 908, a foreground device handler task (DhTaskFor) 912, a telemetry executive task (TlmTaskExec) 914, and a raw data telemetry task (TlmTaskRaw) 916. As generally illustrated in FIG. 9, the background interrogation and foreground device handler tasks 908, 912 provide alternative request paths to the telemetry system 608: a high priority path which handles all foreground telemetry requests (i.e., requests that are initiated by the clinician in the foreground), and a low priority path which handles all background interrogation requests. During automated follow-up, a foreground request is normally generated whenever (i) the clinician departs from the protocol to view a data item that has not yet been retrieved by background interrogation, or (ii) the clinician performs a diagnostic test which makes use of the telemetry channel. All other retrievable data items are read-in using background interrogation.

The executable tasks 902, 904, 908, 912, 914, 916 utilize various data structures (stored within programmer memory) as part of a background/foreground data retrieval protocol. These data structures include a protocol definition structure 920, a raw data shared memory area 922, a raw data status table 926, and a mutual exclusion semaphore 928. The protocol definition structure 922 is generated by the application executive task 902, and specifies the data items that are to be retrieved by background interrogation, including the order for retrieving such items. This data structure 920 is derived from the corresponding protocol definition file (not shown) stored on the programmer hard disk, and includes an ordered list of the protocol items that can be retrieved by background interrogation. (If no protocol has been selected by the clinician, a default protocol definition file which specifies a default retrieval order is used.) In addition, this data structure 920 specifies the sequence of non-protocol data items (if any) that are to be retrieved following the retrieval of the protocol items.

The raw data shared memory area 922 (hereinafter "raw data area") is created and managed by the device handler subsystem 606, and serves as a buffer for the storage of diagnostic and parametric data read from implantable device memory. Following completion of background interrogation, this area 922 contains a duplicate copy of the data stored within the implantable stimulation device 110. (Assuming that the programmer software is configured to retrieve all non-protocol items after the protocol items have been retrieved, all of the retrievable data will reside in programmer memory at this point.) The memory space within the raw data area is pre-allocated (as opposed to being allocated dynamically), such that enough memory is reserved to accommodate the largest possible size of any variable-size data item.

The raw data status table 930 is used by the device handler subsystem 606 to inform the other software components (and particularly the application components) of the retrieval status of the various data items. This table includes a respective entry for each data item stored by the implantable stimulation device 110. Each entry includes the retrieval status of the corresponding data item (READY, INVALID, PENDING, or LOCKED), and includes other information which is specific to the particular data item.

The mutual exclusion semaphore 928 is used to implement a contention protocol between the background and foreground device handler tasks 908, 912, which contend with each other for control of the telemetry subsystem 608. This contention protocol gives priority to foreground requests over background interrogation requests, so that the clinician can interactively perform foreground operations without having to wait for the background interrogation process to be completed. As described below, the contention protocol is implemented in the preferred embodiment such that the foreground task 912 gains control of the telemetry subsystem 608 within 250 milliseconds after a foreground request becomes pending. Thus, from the perspective of the clinician, foreground telemetry operations are performed virtually immediately, without being delayed or interrupted by background interrogation (which is performed transparently to the clinician).

In general operation, the application executive task 902 sends requests (DhRequests) for diagnostic and parametric data items (and requests for other telemetry operations) to the device handler executive task 904, which validates these application-level requests by checking various header information. Provided that the requests are valid, the device handler executive task 904 routes the requests to either the foreground task 912 or the background interrogation task 908, depending upon the type of the request. The background interrogation task 908 only recognizes one type of request, which is a "START BACKGROUND INTERROGATION" request. Upon receiving a "START BACKGROUND INTERROGATION" request, the background interrogation task 908 begins sequentially retrieving all of the data items specified by the protocol definition structure 920, although this background retrieval process may be temporarily interrupted by a pending foreground request. The foreground task 912 supports a full request set, allowing the full range of telemetry operations to be performed in the foreground. Pending foreground requests are held by the foreground task 912 in a request queue 912A, which issues pending telemetry requests on a first-in-first-out basis.

The foreground task 912 and the background interrogation task 908 respond to the application-level requests by generating lower-level requests (TlmRequests) for sub-units of the requested data items. These lower level requests are passed one-at-a-time to the telemetry executive task 914 for processing. (The semaphore-based contention protocol used to control access to the telemetry channel is described below.) The telemetry executive task 914 performs each request (e.g., retrieves the requested data item, or writes the specified data to implantable device memory) to completion, without interruption. Data retrieved from the implantable stimulation device 110 is written to the raw data area 922 by the raw data telemetry task 916. Data items stored within the raw data area 922 are eventually retrieved (and formatted if necessary) by the device handler executive task 904, and are passed to the applications subsystem 604 for display and processing.

As the individual data items are read into memory, the background interrogation and foreground tasks 908, 912 update the raw data status table 930 to reflect the retrieval status of the individual data items. The retrieval status of a given data item can be any one of the following: READY, INVALID, PENDING or LOCKED. The READY state indicates that the data item has been fully retrieved, and can be accessed by an application. The INVALID state indicates that the data item does not reside in programmer memory, and that no request to retrieve the data item has been initiated. The PENDING state indicates that retrieval of the data item has been initiated. The LOCKED state is used to allow tasks to lock out other tasks while the corresponding memory area is being accessed.

The general sequence which occurs when a follow-up protocol is initiated by a clinician will now be described in greater detail. Upon selection of the START PROTOCOL button 304, the application executive task 902 generates the protocol definition structure 920, and then sends a background interrogation request to the device handler executive task 904. The device handler executive task 904 responds by marking the status of each table entry as INVALID, and then issuing a START BACKGROUND INTERROGATION request to the background interrogation task 908. Background data collection thereafter proceeds continuously, unless a foreground telemetry operation is requested before the background interrogation process is completed. If the clinician performs an action (e.g., jumps ahead in the protocol) which requires the use of the telemetry channel, the application executive task generates a foreground request, which is validated and written to the foreground request queue 912A by the device handler executive task 904. As described below, this foreground request is given priority over any pending background interrogation requests.

Prior to retrieving a data item in the background, the background interrogation task 908 checks the status table 930 to ensure that the data item has not already been retrieved in the foreground. Thus, for example, if an event histogram has already been retrieved in the foreground (as reflected by the table 930), the background interrogation task 908 will not duplicate the retrieval, and will simple skip to the next data item of the protocol definition structure 920. For each data item to be retrieved by background interrogation, the background interrogation task 908 generates a series of lower-level telemetry requests (as described above) which correspond to sub-units of the data item. These sub-units of data are sufficiently small in size to ensure that each lower-level telemetry request will be is performed (assuming no data errors) within 250 milliseconds.

Prior to passing each of these lower-level telemetry requests to the telemetry executive task, the background interrogation task "takes" the mutual exclusion semaphore 916 (assuming the semaphore is not being used by the foreground interrogation task 912), or else waits for the semaphore to be relinquished by the foreground task 912. By taking the semaphore, the background interrogation task 908 takes control of the telemetry channel, effectively blocking out the foreground task 912. At the end of each low-level telemetry request, the background interrogation task 908 temporarily relinquishes the semaphore 916, to thereby give the foreground interrogation task 912 an opportunity to take control of the telemetry channel (which it will do if a foreground request is pending). As a result, the foreground interrogation task 912 can be locked out for no more than 250 milliseconds.

The foreground task 912 similarly divides requests for data items into lower-level telemetry requests for sub-units of the data items. However, unlike the background interrogation task 908, the foreground interrogation task 912 does not relinquish the semaphore 916 until the completion all of the lower-level requests associated with the application level request. Foreground operations (such as a request for an event histogram) are thus performed to completion, without being interrupted by the background interrogation task 908.

While certain preferred embodiments of the invention have been described, these embodiments have been presented by way of example only, and are not intended to limit the scope of the present invention. For example, although the description has focused on cardiac implantable devices, it will be appreciated that the programmer features of the invention can be used with other types of implantable medical devices that store diagnostic data, including implantable defibrillators, drug pumps and neural stimulators. In addition, although the invention has been described in the context of a "programmer" it will be recognized that the disclosed automated follow-up features can be embodied within a pure diagnostic system that is not capable of programming the implanted device. Thus, the breadth and scope of the present invention should be defined only in accordance with the following claims and their equivalents.

In the claims which follow, alphabetic characters used to designate claim steps are provided for convenience of description only, and are not intended to imply any particular order for performing the steps.

TABLE 1

| Protocol Step (display screen) | Option #1 | Option #2 | Option #3 | Option #4 | Option #5 | Option #6 | Option #7 | Option #8 |
|---|---|---|---|---|---|---|---|---|
| Stimulation & Sensing Parameters | Skip | *View | Print | View & Print | | | | |
| Timing Parameters | Skip | *View | Print | View & Print | | | | |
| Sensor Parameters | Skip | *View | Print | View & Print | | | | |
| Battery Longevity | Skip | View | Print | *View & Print | | | | |
| Battery Voltage & Impedance | Skip | View | Print | *View & Print | | | | |
| Battery Current | Skip | View | Print | *View & Print | | | | |
| Slaved NIPS | Skip | *Test & Print | | | | | | |
| NIPS | Skip | *Test & Print | | | | | | |
| Quick Check | Skip | View | Print | *View & Print | | | | |
| Event Histogram | Skip | *View | Print | View & Print | Clear | View & Clear | Print & Clear | View, Print & Clear |
| Heart Rate Histogram | Skip | *View | Print | View & Print | Clear | View & Clear | Print & Clear | View, Print & Clear |
| Atrial Rate Histogram | Skip | *View | Print | View & Print | Clear | View & Clear | Print & Clear | View, Print & Clear |
| R wave Histogram | Skip | View | Print | *View & Print | Clear | View & Clear | Print & Clear | View, Print & Clear |
| P wave Histogram | Skip | View | Print | *View & Print | Clear | View & Clear | Print & Clear | View, Print & Clear |
| Sensor Histogram | Skip | View | Print | *View & Print | Clear | View & Clear | Print & Clear | View, Print & Clear |
| ER Polarization Test | Skip | *Test & Print | | | | | | |
| ER Sensitivity Test | Skip | *Test & Print | | | | | | |
| Vent Capture Test | Skip | *Test & Print | | | | | | |
| Atrial Capture Test | Skip | *Test & Print | | | | | | |
| Vent Sense Test | Skip | *Test & Print | | | | | | |
| Atrial Sense Test | Skip | *Test & Print | | | | | | |
| Strength Duration Test | Skip | *Test & Print | | | | | | |
| Retrograde Conduction Test | Skip | *Test & Print | | | | | | |
| Long Term Threshold Record | Skip | View | Print | *View & Print | | | | |
| 7-Day Threshold Record | Skip | View | Print | *View & Print | | | | |
| Loss Of Capture Log | Skip | View | Print | *View & Print | | | | |
| Threshold Histog ram | Skip | View | Print | *View & Print | | | | |
| Stimulation Histogram | Skip | View | Print | *View & Print | | | | |
| Threshold Search Difference Histogram | Skip | View | Print | *View & Print | | | | |

TABLE 1-continued

| Protocol Step (display screen) | Option #1 | Option #2 | Option #3 | Option #4 | Option #5 | Option #6 | Option #7 | Option #8 |
|---|---|---|---|---|---|---|---|---|
| Atrial Lead Measurements | Skip | View | Print | *View & Print | | | | |
| Auto Set | Skip | *Test & Print | | | | | | |
| Rate Prediction | Skip | *Test & Print | | | | | | |
| Auto Mode Switch Log | Skip | View | Print | *View & Print | | | | |
| Rhythm Log | Skip | *View | Print | View & Print | | | | |
| Event Record | Skip | View | Print | *View & Print | | | | |
| Event Snapshots | Skip | *View | Print | View & Print | | | | |
| IEGM Snapshots | Skip | View | Print | *View & Print | | | | |
| Event Bar Graph | Skip | View | Print | *View & Print | | | | |
| Rate Bar Graph | Skip | View | Print | *View & Print | | | | |
| Sensor Bar Graph | Skip | View | Print | *View & Print | | | | |
| AV Delay Bar Graph | Skip | View | Print | *View & Print | | | | |
| Patient Data | Skip | View | Print | *View & Print | | | | |
| Clear All Diagnostics Data | Skip | View | Print | *View & Print | | | | |
| Send Data To Database | Skip | *View | | | | | | |
| Final Summary | Skip | View | Print | *View & Print | | | | |
| End Session | Skip | *View | | | | | | |

What is claimed is:

1. A method of facilitating the rapid examination of a patient that has an implanted medical device, the medical device storing a plurality of diagnostic data records which may be selectively retrieved by an external diagnostic system and displayed via a plurality of corresponding preformatted display screens of the diagnostic system, the method comprising the steps of:

(a) presenting a clinician with at least one menu screen to allow the clinician to specify at least (i) a set of diagnostic data records to be retrieved and displayed by the diagnostic system during a follow-up session with a patient, the set including at least two different diagnostic data records which correspond to at least two different display screens of the diagnostic system, and (ii) a viewing order for the display of the diagnostic data records of the set by the diagnostic system;

(b) recording the set and viewing order specified by the clinician in step (a) for subsequent use as at least a part of a custom follow-up protocol;

thereafter, in response to clinician initiation of the custom follow-up protocol:

(c) automatically retrieving the diagnostic data records of the set from the implanted medical device with the diagnostic system; and (d) displaying the diagnostic data records of the set via corresponding display screens in the clinician-specified viewing order.

2. The method according to claim 1, wherein steps (c) and (d) are performed concurrently, so that the clinician can begin viewing some of the diagnostic data records of the set while other diagnostic data records of the set are being retrieved in the background by the diagnostic system.

3. The method according to claim 2, wherein step (c) comprises the steps of:

automatically analyzing the diagnostic data records; and interrupting the clinician-specified viewing order based on the analysis of the diagnostic data records.

4. The method according to claim 3, wherein the analyzing step comprises the step of detecting a significant change in lead impedance.

5. The method according to claim 3, wherein the analyzing step comprises the step of detecting loss of capture.

6. The method according to claim 3, wherein the analyzing step comprises the step of detecting a low battery condition.

7. The method according to claim 3, wherein the analyzing step comprises the step of detecting a component failure.

8. The method according to claim 1, wherein step (c) comprises the step of:

retrieving the diagnostic data records of the set in the viewing order specified by the clinician so that a given diagnostic data record of the set will be retrieved before the clinician attempts to view the diagnostic data record.

9. The method according to claim 1, further comprising the steps of:

automatically storing all initial programmed settings;
automatically storing all final programmed settings;
comparing the initial programmed settings to the final programmed setting; and
displaying a summary of the changes in programmed settings.

10. The method according to claim 1, wherein the set is a subset of the plurality of diagnostic data records stored by the implanted medical device, the method further comprising the step of:

automatically retrieving from the medical device at least some of the diagnostic data records that are not part of the clinician-specified set, to thereby enable the clinician to view additional diagnostic data records that are not part of the custom protocol without having to wait for the retrieval by the diagnostic system of the additional diagnostic data records.

11. The method according to claim 1, further comprising the steps of:

(e) presenting the clinician with a menu screen to allow the clinician to specify a printing order for the printing of at least some of the diagnostic data records of the set;

(f) recording the printing order as part of the custom follow-up protocol; and (g) in response to clinician initiation of the custom follow-up protocol, automatically printing the diagnostic data records designated in step (e) in the printing order specified by the clinician.

12. The method according to claim 11, wherein step (e) comprises the step of:

presenting the clinician with a menu screen which allows the clinician to specify a printing order which is different from the viewing order.

13. The method according to claim 1, wherein step (d) comprises the step of:

presenting the clinician with a user interface button which allows the clinician to interactively sequence through the diagnostic data records of the protocol in the viewing order.

14. The method according to claim 1, wherein step (a) comprises the steps of:

presenting the clinician with a list of predefined protocol steps that can selectively be included by the clinician in the custom protocol; and presenting menu options which allow the clinician to create a subset of the list, at least some of the predefined protocol steps comprising retrieval of diagnostic data records from the implanted medical device.

15. The method according to claim 14, wherein at least one of the protocol steps of the list comprises a diagnostic test to be performed during the follow-up session using the implanted medical device.

16. The method according to claim 14, wherein at least one of the protocol steps of the list comprises a retrieval of a set of control parameters, the control parameters controlling a therapy protocol of the implanted medical device.

17. The method according to claim 1, wherein at least one of the diagnostic data records comprises a selected one of a histogram, a rhythm log, a capture test data, a sensitivity test data, and a physiological sensor data.

18. The method according to claim 1, wherein the step (b) of recording the set and viewing order specified by the clinician comprises the step of recording the set and viewing order in the implanted medical device.

19. The method according to claim 1, wherein the step (b) of recording the set and viewing order specified by the clinician comprises the step of recording the set and viewing order in the external diagnostic system.

20. A method of enabling a clinician to perform a customized examination of a patient that has an implanted medical device, the medical device storing diagnostic data records which can be retrieved by an external diagnostic system and displayed on a display monitor of the diagnostic system via corresponding preformatted display screens, the method comprising the steps of:

(a) presenting the clinician with at least one menu screen which allows the clinician to specify a custom protocol via a user interface of the diagnostic system, the custom protocol including a clinician-specified plurality of display screens to be displayed by the diagnostic system during sessions with the patient and with other patients, and including a clinician-specified viewing order for the display by the diagnostic system of the plurality of display screens, at least some of the plurality of display screens corresponding to respective diagnostic data records stored within the medical device;

(b) recording the custom protocol for subsequent use;

thereafter, in response to initiation by the clinician of the custom protocol during a session with the patient;

(c) automatically retrieving from the implanted medical device a plurality of diagnostic data records which correspond to the plurality of display screens, the step of automatically retrieving requiring no user interaction with the diagnostic system; and (d) displaying the plurality of diagnostic data records on the monitor via the plurality of display screens in the viewing order of the custom protocol, the step of displaying comprising presenting the clinician with an input button which, when selected by the clinician, causes a next sequential display screen of the custom protocol to be displayed.

21. The method according to claim 20, wherein at least some of the plurality of display screens of the custom protocol screens correspond to respective diagnostic tests to be performed during the session using the implanted medical device.

22. The method according to claim 20, wherein steps (c) and (d) are performed concurrently, so that the clinician can begin viewing some of the diagnostic data records of the custom protocol while other diagnostic data records of the protocol are being retrieved by the diagnostic system.

23. The method according to claim 22, wherein step (c) further comprises the steps of:

automatically analyzing the diagnostic data records; and interrupting the clinician-specified viewing order based on the analysis of the diagnostic data records.

24. The method according to claim 20, wherein step (c) comprises retrieving at least some of the plurality of diagnostic data records in an order which corresponds to the viewing order specified by the clinician, to thereby increase a likelihood that a given diagnostic data record will be retrieved before the clinician attempts to view a corresponding display screen.

25. The method according to claim 20, wherein step (c) comprises repetitively interrogating the implanted medical device to successively retrieve the plurality of diagnostic data records.

26. The method according to claim 20, further comprising the step of temporarily interrupting the automatic retrieval in step (c) of the plurality of diagnostic data records to allow the clinician to conduct a diagnostic test using the implanted medical device.

27. The method according to claim 20, wherein the custom protocol further comprises a clinician-specified print order for the printing of at least some of the plurality of display screens, and wherein the print order is different from the viewing order.

28. The method according to claim 22, further comprising the steps of:

automatically storing all initial programmed settings;

automatically storing all final programmed settings;

comparing the initial programmed settings to the final programmed setting; and displaying a summary of the changes in programmed settings.

29. A method of facilitating an examination by a clinician of a patient that has an implanted medical device, the medical device storing diagnostic data which may be retrieved by an external diagnostic system and displayed on a screen of the diagnostic system, the method comprising the steps of:

(a) enabling the clinician, via a user interface of the diagnostic system, to specify a plurality of protocol steps to be performed during an examination session with a patient, and to specify an order for performing the plurality of protocol steps, each of the protocol steps including at least (i) an interrogation of the implanted medical device with the diagnostic system, and (ii) a display of data associated with the interrogation to the clinician by the diagnostic system;

(b) recording the plurality of protocol steps specified by the clinician in step (a) for subsequent use as a custom examination protocol or a portion thereof; and (c) in response to clinician initiation of the custom examination protocol via the user interface, automatically performing the protocol steps of the custom protocol in the clinician-specified order.

30. The method according to claim 29, wherein at least some of the protocol steps include (i) a retrieval by the diagnostic system of a respective diagnostic data record stored within the implanted medical device, and (ii) a subsequent display of the diagnostic data record on the screen of the diagnostic system.

31. The method according to claim 29, wherein at least some of the protocol steps include respective diagnostic tests.

32. The method according to claim 29, wherein step (c) comprises displaying a sequence of preformatted data display screens to the clinician in a viewing order which corresponds to the order specified in step (a).

33. The method according to claim 32, wherein step (c) further comprises the step of:

enabling the clinician via the user interface to step through the sequence of data display screens in the viewing order by selecting a protocol advance button of the user interface, selection of the protocol advance button causing a next data display screen of the custom examination protocol to be displayed.

34. The method according to claim 33, wherein step (c) further comprises the steps of:

(i) presenting the clinician with at least one menu option which allows the clinician to temporarily depart from the custom examination protocol to view a data display screen which is not part of the protocol; and (ii) when the clinician departs from the protocol, presenting the clinician with a menu option which allows the clinician to return to the protocol at a point of departure.

35. The method according to claim 29, wherein step (c) comprises the steps of:

automatically analyzing the interrogated data; and interrupting the clinician-specified order based on the analysis of the data.

36. The method according to claim 29, further comprising the steps of:

automatically storing all initial programmed settings;

automatically storing all final programmed settings;

comparing the initial programmed settings to the final programmed setting; and displaying a summary of the changes in programmed settings.

37. The method according to claim 29, wherein at least one of the protocol steps includes (i) an automatic retrieval by the diagnostic system of a histogram stored within the medical device, and (ii) a display of the histogram on the screen of the diagnostic system.

38. The method according to claim 36, wherein the at least one protocol step further includes automatically clearing the histogram from a memory of the implanted medical device.

39. A diagnostic system for facilitating a customized examination of a patient having an implanted medical device, the implanted medical device storing diagnostic data which is retrieved and displayed by the diagnostic system during the examination of the patient, the diagnostic system comprising:

a computer processor operatively coupled to a memory and a display monitor;

telemetry circuitry operatively coupled to the computer processor, the telemetry circuitry enabling the computer processor to communicate with the implanted device over a wireless telemetry link; and diagnostic software stored in the memory, the diagnostic software including:

(a) custom protocol definition software for allowing clinicians to define and record custom examination protocols, the custom protocol definition software configured to display a plurality of available follow-up examination steps that correspond to the implantable medical device, and to allow a clinician to define a custom examination protocol which comprises (i) a clinician-specified subset of the plurality of available examination steps, and (ii) a clinician-specified order for performing the examination steps of the subset; and (b) protocol execution software which, in response to clinician initiation of the custom examination protocol, (i) automatically retrieves diagnostic data corresponding to the clinician-specified subset from the implanted medical device, and (ii) displays a plurality of display screens on the display monitor in a viewing order which corresponds to the clinician-specified order.

40. The diagnostic system according to claim 39, wherein the protocol execution software automatically retrieves the diagnostic data in an order which corresponds to the clinician-specified order.

41. The diagnostic system according to claim 39, wherein the protocol execution software displays a protocol advance button on the display screen, the protocol advance button allowing a clinician to sequence through the plurality of display screens in the viewing order.

42. The diagnostic system according to claim 39, wherein each examination step of the plurality of available examination steps includes a respective communication between the diagnostic system and the implanted device.

43. The diagnostic system according to claim 39, wherein the diagnostic software further comprises:

(c) a protocol library which includes at least one standard examination protocol, and which stores custom examination protocols defined via the custom protocol definition software; and (d) protocol selection software which enables a clinician to selectively initiate examination protocols stored within the protocol library.

44. The diagnostic system according to claim 39, wherein at least two of the plurality of display screens correspond to respective diagnostic data records retrieved by the diagnostic system.

45. The diagnostic system according to claim 39, wherein the protocol execution software is configured to allow the clinician to examinarily depart from the custom examination protocol.

46. The diagnostic system according to claim 39, wherein the protocol execution software is configured to retrieve diagnostic data in the background while concurrently allowing the clinician to view and sequence through the display screens of the protocol.

47. The diagnostic system according to claim 39, wherein the custom protocol definition software further allows the clinician to define a print order for the printing of diagnostic data retrieved from the implanted medical device.

48. A method of facilitating the rapid examination of a patient that has an implanted medical device, the implanted medical device storing diagnostic data records which may be retrieved and displayed by an external diagnostic system, the method comprising the steps of:

(a) presenting a clinician with at least one menu screen of a graphical user interface of the diagnostic system to allow the clinician to select a pre-specified examination protocol, the examination protocol specifying at least an order for the retrieval of the plurality of diagnostic data records from the implanted medical device;

(b) successively retrieving the plurality of diagnostic data records from the implanted medical device into the diagnostic system in the order specified by the examination protocol without requiring clinician intervention, the step of successively retrieving comprising successively interrogating the implanted medical device with the diagnostic system to specify diagnostic data records to be retrieved; and (c) concurrently with step (b), allowing the clinician to view the diagnostic data records that have been retrieved in step (b) on a screen of the diagnostic system while the diagnostic system continues to retrieve the remaining diagnostic data records of the plurality;

whereby the method enables the clinician to begin evaluation of some diagnostic data records while other diagnostic data records are being retrieved in the background by the diagnostic system.

49. The method according to claim 48, wherein step (c) comprises the step of:

presenting an ordered plurality of display screens to the clinician via the graphical user interface, the ordered plurality of display screens corresponding to the examination protocol and the plurality of diagnostic data records.

50. The method according to claim 48, further comprising the steps of:

(d) during steps (b) and (c), monitoring clinician input to the diagnostic system to determine whether the clinician has departed from a default viewing order of the examination protocol; and (e) when the clinician has departed from the default viewing order, temporarily interrupting the successive retrieval in step (b) and retrieving a diagnostic data record which corresponds to the clinician's departure from the protocol;

the method thereby dynamically adjusting an automatic data retrieval order to correspond to an actual viewing order followed by the clinician.

51. The method according to claim 48, further comprising the steps of:

(d) during steps (b) and (c), monitoring clinician input to the diagnostic system to determine whether a diagnostic test of the evaluation protocol has been reached; and (e) when the diagnostic test has been reached, temporarily interrupting the successive retrieval in step (b) to allow the diagnostic test to be performed.

52. The method according to claim 48, further comprising the steps of:

(d) after the plurality of diagnostic data records have been retrieved in step (b), automatically retrieving a plurality of additional diagnostic data records from the implanted medical device.

53. The method according to claim 52, further comprising the step of storing all diagnostic data records retrieved in steps (b) and (d) in a session log for subsequent retrieval and evaluation.

54. The method according to claim 48, wherein the pre-specified examination protocol is a custom examination protocol defined by the clinician.

55. The method according to claim 48, wherein the pre-specified examination protocol is a non-custom examination protocol provided as a standard component of the diagnostic system.

56. The method according to claim 48, wherein step (b) is performed automatically in response to initiation by the clinician of the pre-specified examination protocol.

57. A diagnostic system for allowing a clinician to rapidly conduct an examination of a patient having an implanted medical device, the implanted medical device storing a plurality of diagnostic data records which may be selectively retrieved and displayed by the diagnostic system, the diagnostic system comprising:

a computer processor operatively coupled to a memory and a display monitor;

telemetry circuitry operatively coupled to the computer processor, the telemetry circuitry enabling the computer processor to communicate with the implanted medical device over a wireless telemetry link;

an examination protocol specification stored within the memory, the examination protocol comprising a plurality of data retrieval steps for the retrieval of respective diagnostic data records from the implanted device, the examination protocol further comprising a viewing order for the display of the diagnostic data records on the display monitor;

data retrieval software stored within the memory, the data retrieval software configured to automatically retrieve the diagnostic data records of the examination protocol; and protocol display software stored within the memory, the protocol display software configured to display the diagnostic data records retrieved by the data retrieval software in the viewing order of the examination protocol.

58. The diagnostic system according to claim 57, wherein the protocol display software and the data retrieval software are configured to operate concurrently, so that a clinician can begin viewing diagnostic data records that have been retrieved while other diagnostic data records of the protocol are being retrieved in the background.

59. The diagnostic system according to claim 58, wherein the data retrieval software is configured to retrieve the diagnostic data records of the protocol in the viewing order, to thereby increase a likelihood that each individual diagnostic data record of the examination protocol will be retrieved before the clinician attempts to view the diagnostic data record.

60. The diagnostic system according to claim 57, wherein the protocol display software allows a clinician to sequence through the diagnostic data records in the viewing order by repetitively activating a protocol advance button.

61. The diagnostic system according to claim 57, wherein the protocol display software allows a clinician to selectively depart from and return to the examination protocol while viewing the diagnostic data records of the protocol.

62. The diagnostic system according to claim 57, wherein at least one of the diagnostic data records of the examination protocol is a heart rate histogram.

63. The diagnostic system according to claim 57, further comprising custom protocol generation software for allowing a clinician to define a custom examination protocol and store the custom examination protocol within the memory for subsequent use.

64. The diagnostic system according to claim 57, wherein the examination protocol further comprises a plurality of diagnostic tests.

65. A user interface for facilitating the rapid, customized viewing of diagnostic data records retrieved from an implanted medical device by a diagnostic system, the diagnostic system including a display monitor for the display of the diagnostic data records, the user interface implemented by executable code stored on a computer readable medium, the user interface comprising:

a plurality of preformatted data display screens which correspond to a plurality of protocol steps, at least some of the plurality of protocol steps comprising a retrieval and display by the diagnostic system of respective diagnostic data records stored by the implanted medical device; and at least one customization screen which allows a clinician to pre-specify at least a viewing order for the display by the diagnostic system of the plurality of preformatted data display screens.

66. The user interface according to claim 65, further comprising a display screen advance button which, following retrieval by the diagnostic system of the plurality of diagnostic data records, allows a clinician to sequence through the plurality of display screens in the prespecified viewing order to view the diagnostic data records.

67. The user interface according to claim 65, further comprising at least one control button which enables the clinician to temporarily depart from the pre-specified viewing order when viewing the plurality of diagnostic data records.

68. The user interface according to claim 65, wherein at least one of the plurality of preformatted data display screens corresponds to a histogram stored by the implanted medical device.

69. The user interface according to claim 65, wherein each preformatted data display screen occupies a window of the user interface.

70. A software architecture for facilitating the rapid and efficient examination of a patient that has an implanted medical device, the medical device storing diagnostic data records which can selectively be retrieved and viewed using an external diagnostic system, the diagnostic system communicating with the implanted device over a telemetry channel, the architecture including:

application-level software stored on a computer-readable medium, the application-level software permitting a clinician to initiate a background interrogation operation in which the diagnostic system automatically retrieves and buffers at least a pre-specified plurality of the diagnostic data records for subsequent viewing by the clinician, the application-level software also permitting the clinician to initiate a foreground operation in which the diagnostic system retrieves and displays a clinician-specified diagnostic data record; and telemetry software stored on the computer-readable medium, the telemetry software configured to retrieve diagnostic data items from the implanted device into a memory of the diagnostic system in response to clinician initiation of background interrogation operations and foreground operations, the telemetry software implementing a telemetry channel contention protocol, the contention protocol giving priority to pending foreground operations over ongoing background interrogation operations so that foreground operations are performed immediately from the perspective of the clinician.

71. The software architecture as in claim 70, wherein the telemetry software includes:

a background interrogation software task configured to retrieve the pre-specified plurality of the diagnostic data records over the telemetry channel in response to clinician initiation of the background interrogation operation; and a foreground software task configured to retrieve the clinician-specified diagnostic data record over the telemetry channel in response to clinician-initiation of the foreground operation;

and wherein the telemetry channel contention protocol gives priority to pending foreground operations over ongoing background interrogation operations by preventing the background interrogation task from using the telemetry channel while a foreground operation is pending.

72. The software architecture as in claim 70, wherein the application-level software includes a protocol definition module for allowing the clinician to generate and store a protocol definition data structure, the protocol definition structure specifying at least a default viewing order for the display of diagnostic data items retrieved as part of a background interrogation operation.

* * * * *